(12) United States Patent
Potter et al.

(10) Patent No.: US 6,740,322 B2
(45) Date of Patent: May 25, 2004

(54) IMMUNIZATION OF DAIRY CATTLE WITH MIG PROTEIN

(75) Inventors: Andrew A. Potter, Saskatoon (CA); Alexandra J. Bolton, Calgary (CA); Xin Ming Song, Saskatoon (CA)

(73) Assignee: University of Saskatchewan, Saskatchewan (CA)

( * ) Notice: Subject to any disclaimer, the term of this patent is extended or adjusted under 35 U.S.C. 154(b) by 0 days.

(21) Appl. No.: 09/878,756

(22) Filed: Jun. 11, 2001

(65) Prior Publication Data

US 2002/0025322 A1 Feb. 28, 2002

Related U.S. Application Data

(60) Provisional application No. 60/211,016, filed on Jun. 12, 2000.

(51) Int. Cl.$^7$ .................. A61K 39/00; A61K 39/02; A61K 39/09; C07K 1/00
(52) U.S. Cl. ............... 424/185.1; 424/190.1; 424/234.1; 424/244.1; 530/350
(58) Field of Search ............ 424/185.1, 190.1, 424/234.1, 244.1; 530/350

(56) References Cited

U.S. PATENT DOCUMENTS

| | | |
|---|---|---|
| 4,493,825 A | 1/1985 | Platt et al. |
| 4,954,618 A | 9/1990 | Fahnestock et al. |
| 4,977,082 A | 12/1990 | Boyle et al. |
| 5,237,050 A | 8/1993 | Boyle et al. |
| 5,328,987 A | 7/1994 | Maliszewski |
| 5,328,996 A | 7/1994 | Boyle et al. |
| 5,721,339 A | 2/1998 | Boyle et al. |
| 5,863,543 A | 1/1999 | Jiang et al. |
| 6,100,055 A | * 8/2000 | Guss et al. |

OTHER PUBLICATIONS

Plotkin et al. (Vaccines W.B. Saunders Co. Philadelphia p. 571), 1988.*
Baird et al., "Epitopes of Group a Streptococcal M Protein Shared With Antigens of Articular Cartilage and Synovium," *The Journal of Immunology* 146(9):3132–3137 (1991).
Bisno, Alan. L., "Group A. Streptococcal Infections and Acute Rheumatic Fever," *New Eng J. Med.* 325:783–793 (1991).
Bronze et al., "Epitopes of Streptococcal M Proteins that Evoke Antibodies That Cross–React with Human Brain," *The Journal of Immunology* 151(5):2820–2828 (1993).
Cunningham et al., "Study of Heart–Reactive Antibody in Antisera and Hybridoma Culture Fluids Against Group A Streptococci," *Infection and Immunity* 42(2):531–538 (1983).
Dale and Beachy, "Protective Antigenic Determinant of Streptococcal M Protein Shared With Sarcolemmal Membrane Protein of Human Heart," *J. Exp. Med.* 156:1165–1176 (1982).
Dale and Beachy, "Multiple, Heart–Cross Reactive Epitopes of Streptococcal M Proteins," *J. Exp. Med.* 161:113–122 (1995).
Froude et al., "Cross–Reactivity Between Streptococcus and Human Tissue: A Model of Molecular Mimicry and Autoimmunity," *Microbiology and Immunology* 145:6–26 (1989).
Jonsson et al., "The type–III Fc Receptor for Streptococcus Dysgalactiae is Also an Alpha2–Macroglobulin Receptor," *European Journal of Biochemistry* 220:819–826 (1994).
Kehoe, Michael A., "Group A Streptococcal Antigens and Vaccine Potential," *Vaccine* 9:797–806 (1991).
Lancefield, Rebecca C., "Current Knowledge of Type–Specific M Antigens of Group A Streptococci," *J. of Immunology* 89:307–313 (1962).
Langone, John J., j"Protein A of *Staphylococcus aureus* and Related Immunoglobulin Receptors Produced by Streptococci and Pneumonococci," *Advances in Immunology* 32:167 (1982).
Liljeqvist et al., "Surface Display of Functional Fibronectin–Binding Domains on *Staphylococcus carnosus*," *FEBS Letters* 446:299–304 (1999).
Stollerman, Gene H., "Rheumatogenic Streptococci and Autoimmunity," *Clinical Immunology and Immunopathology* 61:131–142 (1991).
Vasi et al., "Five Homologous Repeats of the Protein G–Related Protein MIG Cooperate in Binding to Goad Immunoglobulin G," *Infection and Immunity* 67(1):413–416 (1999).
Yarnall et al., "Antibody Response to Haemophilus Somnus Fc Receptor," *Journal of Clinical Microbiology* 27(1):111–117 (1989).

* cited by examiner

Primary Examiner—Mark Navarro
(74) Attorney, Agent, or Firm—Robins & Pasternak LLP

(57) ABSTRACT

The Mig protein gene of *Streptococcus dysgalactiae*, and the corresponding amino acid sequence, is described, as is the use of the Mig protein in vaccine compositions to prevent and treat bacterial infections in general, and mastitis in particular.

4 Claims, 9 Drawing Sheets

| | | | | | | | | | | | | | | | | |
|---|---|---|---|---|---|---|---|---|---|---|---|---|---|---|---|---|
| atg | gaa | aaa | gaa | aaa | aaa | gta | aaa | tac | ttt | tta | cgt | aaa | tca | gct | ttt | 48 |
| Met | Glu | Lys | Glu | Lys | Lys | Val | Lys | Tyr | Phe | Leu | Arg | Lys | Ser | Ala | Phe | |
| 1 | | | | 5 | | | | | 10 | | | | | 15 | | |
| gga | tta | gcg | tct | gta | tca | gct | gcg | ttt | tta | gtt | tcg | gga | gca | cta | gaa | 96 |
| Gly | Leu | Ala | Ser | Val | Ser | Ala | Ala | Phe | Leu | Val | Ser | Gly | Ala | Leu | Glu | |
| | | | | 20 | | | | | 25 | | | | | 30 | | |
| aat | act | ata | act | gtt | tct | gca | gaa | act | ata | cct | gca | gcg | gtc | att | gta | 144 |
| Asn | Thr | Ile | Thr | Val | Ser | Ala | Glu | Thr | Ile | Pro | Ala | Ala | Val | Ile | Val | |
| | | 35 | | | | | 40 | | | | | 45 | | | | |
| cct | gtt | ggc | cta | gat | act | aca | gaa | tta | caa | aaa | tgg | tat | gac | att | gca | 192 |
| Pro | Val | Gly | Leu | Asp | Thr | Thr | Glu | Leu | Gln | Lys | Trp | Tyr | Asp | Ile | Ala | |
| | 50 | | | | | 55 | | | | | 60 | | | | | |
| aat | gat | tta | gtt | gcg | act | gac | aat | gct | act | ccg | gga | ggc | gta | ttt | aca | 240 |
| Asn | Asp | Leu | Val | Ala | Thr | Asp | Asn | Ala | Thr | Pro | Gly | Gly | Val | Phe | Thr | |
| 65 | | | | | 70 | | | | | 75 | | | | | 80 | |
| gca | gac | tca | atg | aag | gca | tta | tat | cgt | tta | cta | aat | gat | gca | tac | gat | 288 |
| Ala | Asp | Ser | Met | Lys | Ala | Leu | Tyr | Arg | Leu | Leu | Asn | Asp | Ala | Tyr | Asp | |
| | | | | 85 | | | | | 90 | | | | | 95 | | |
| gtg | ttg | gaa | tca | aaa | gac | tat | aga | aaa | tat | gat | tct | caa | gat | agg | att | 336 |
| Val | Leu | Glu | Ser | Lys | Asp | Tyr | Arg | Lys | Tyr | Asp | Ser | Gln | Asp | Arg | Ile | |
| | | | | 100 | | | | | 105 | | | | | 110 | | |
| gtt | gaa | ttg | gta | aac | aat | tta | aag | aat | act | acg | cag | tct | ctt | tta | cca | 384 |
| Val | Glu | Leu | Val | Asn | Asn | Leu | Lys | Asn | Thr | Thr | Gln | Ser | Leu | Leu | Pro | |
| | | | | 115 | | | | | 120 | | | | | 125 | | |
| att | gga | gta | gaa | cca | gta | gta | ttt | gat | act | act | cgc | ttg | aat | acc | tgg | 432 |
| Ile | Gly | Val | Glu | Pro | Val | Val | Phe | Asp | Thr | Thr | Arg | Leu | Asn | Thr | Trp | |
| | | | | 130 | | | | | 135 | | | | | 140 | | |
| tat | gat | gct | gct | aat | gaa | att | gtt | aat | aat | tca | gat | gct | tat | aca | gca | 480 |
| Tyr | Asp | Ala | Ala | Asn | Glu | Ile | Val | Asn | Asn | Ser | Asp | Ala | Tyr | Thr | Ala | |
| 145 | | | | | 150 | | | | | 155 | | | | | 160 | |
| gaa | tca | att | cag | tcg | ttg | tat | aag | tta | att | aat | gat | gca | tac | gat | gtg | 528 |
| Glu | Ser | Ile | Gln | Ser | Leu | Tyr | Lys | Leu | Ile | Asn | Asp | Ala | Tyr | Asp | Val | |
| | | | | 165 | | | | | 170 | | | | | 175 | | |
| tta | gaa | tca | aaa | gat | tac | agt | aag | tat | gat | tct | caa | gat | aaa | gtc | aac | 576 |
| Leu | Glu | Ser | Lys | Asp | Tyr | Ser | Lys | Tyr | Asp | Ser | Gln | Asp | Lys | Val | Asn | |
| | | | | 180 | | | | | 185 | | | | | 190 | | |
| aat | ctt | gca | gat | cag | ttg | aga | gat | gca | gtt | cag | gca | gtt | caa | cta | gaa | 624 |
| Asn | Leu | Ala | Asp | Gln | Leu | Arg | Asp | Ala | Val | Gln | Ala | Val | Gln | Leu | Glu | |
| | | 195 | | | | | 200 | | | | | 205 | | | | |

FIG. 1A

```
gca cct aca gtg att gac gca cct gaa cta act cca gct ttg act act    672
Ala Pro Thr Val Ile Asp Ala Pro Glu Leu Thr Pro Ala Leu Thr Thr
    210                 215                 220 tac aaa ctt gtt gtt aaa ggt aac act ttc tca gga gaa aca act act    720
Tyr Lys Leu Val Val Lys Gly Asn Thr Phe Ser Gly Glu Thr Thr Thr
225                 230                 235                 240 aaa gcc atc gat act gca act gcg gaa aaa gaa ttc aaa caa tac gca    768
Lys Ala Ile Asp Thr Ala Thr Ala Glu Lys Glu Phe Lys Gln Tyr Ala
                245                 250                 255 aca gct aac aat gtt gac ggt gag tgg tct tat gac gat gca act aaa    816
Thr Ala Asn Asn Val Asp Gly Glu Trp Ser Tyr Asp Asp Ala Thr Lys
            260                 265                 270 acc ttt aca gtt act gaa aaa cca gca gtg att gac gca ctt gaa cta    864
Thr Phe Thr Val Thr Glu Lys Pro Ala Val Ile Asp Ala Leu Glu Leu
        275                 280                 285 act cca gcc ttg act act tac aaa ctt att gtt aaa ggt aac act ttc    912
Thr Pro Ala Leu Thr Thr Tyr Lys Leu Ile Val Lys Gly Asn Thr Phe
    290                 295                 300 tca ggc gaa aca act act aaa gct atc gat gct gca act gca gaa aaa    960
Ser Gly Glu Thr Thr Thr Lys Ala Ile Asp Ala Ala Thr Ala Glu Lys
305                 310                 315                 320 gaa ttc aaa caa tac gca aca gct aac aat gtt gac ggt gag tgg tct   1008
Glu Phe Lys Gln Tyr Ala Thr Ala Asn Asn Val Asp Gly Glu Trp Ser
                325                 330                 335 tat gac tat gca act aaa acc ttt aca gtt act gaa aaa cca gca gtg   1056
Tyr Asp Tyr Ala Thr Lys Thr Phe Thr Val Thr Glu Lys Pro Ala Val
            340                 345                 350 att gac gca cct gaa cta act cca gcc ttg act act tac aaa ctt att   1104
Ile Asp Ala Pro Glu Leu Thr Pro Ala Leu Thr Thr Tyr Lys Leu Ile
        355                 360                 365 gtt aaa ggt aac act ttc tca ggc gaa aca act act aaa gct atc gat   1152
Val Lys Gly Asn Thr Phe Ser Gly Glu Thr Thr Thr Lys Ala Ile Asp
    370                 375                 380 gct gca act gca gaa aaa gaa ttc aaa caa tac gca aca gct aac aat   1200
Ala Ala Thr Ala Glu Lys Glu Phe Lys Gln Tyr Ala Thr Ala Asn Asn
385                 390                 395                 400 gtt gac ggt gaa tgg tct tat gac gat gca act aaa acc ttt aca gtt   1248
Val Asp Gly Glu Trp Ser Tyr Asp Asp Ala Thr Lys Thr Phe Thr Val
                405                 410                 415
```

FIG. 1B

```
act gaa aaa cca gca gtg att gac gca cct gaa cta act cca gcc ttg    1296
Thr Glu Lys Pro Ala Val Ile Asp Ala Pro Glu Leu Thr Pro Ala Leu
            420                 425                 430 act act tac aaa ctt att gtt aaa ggt aac act ttc tca ggc gaa aca    1344
Thr Thr Tyr Lys Leu Ile Val Lys Gly Asn Thr Phe Ser Gly Glu Thr
            435                 440                 445 act act aaa gca gta gac gca gaa act gca gaa aaa gcc ttc aaa caa    1392
Thr Thr Lys Ala Val Asp Ala Glu Thr Ala Glu Lys Ala Phe Lys Gln
        450                 455                 460 tac gca aca gct aac aat gtt gac ggt gaa tgg tct tat gac gat gca    1440
Tyr Ala Thr Ala Asn Asn Val Asp Gly Glu Trp Ser Tyr Asp Asp Ala
465             470                 475                 480 act aaa acc ttt aca gtt act gaa aaa cca gca gtg att gac gca cct    1488
Thr Lys Thr Phe Thr Val Thr Glu Lys Pro Ala Val Ile Asp Ala Pro
                485                 490                 495 gaa tta aca cca gca ttg aca acc tac aaa ctt gtt atc aat ggt aaa    1536
Glu Leu Thr Pro Ala Leu Thr Thr Tyr Lys Leu Val Ile Asn Gly Lys
            500                 505                 510 aca ttg aaa ggc gaa aca act act aaa gca gta gac gta gaa act gca    1584
Thr Leu Lys Gly Glu Thr Thr Thr Lys Ala Val Asp Val Glu Thr Ala
        515                 520                 525 gaa aaa gcc ttc aaa caa tac gct aac gaa aac ggt gtt gat ggt gtt    1632
Glu Lys Ala Phe Lys Gln Tyr Ala Asn Glu Asn Gly Val Asp Gly Val
    530                 535                 540 tgg act tac gat gat gcg act aag acc ttt acg gta act gaa atg gtt    1680
Trp Thr Tyr Asp Asp Ala Thr Lys Thr Phe Thr Val Thr Glu Met Val
545             550                 555                 560 act gaa att cct ggt gat gca cca act gaa cca gaa aag cca gaa gca    1728
Thr Glu Ile Pro Gly Asp Ala Pro Thr Glu Pro Glu Lys Pro Glu Ala
                565                 570                 575 agt atc cct ctt gtt ccg tta act cct gca act cca att gct aaa gat    1776
Ser Ile Pro Leu Val Pro Leu Thr Pro Ala Thr Pro Ile Ala Lys Asp
            580                 585                 590 gac gct aag aaa gac gat act aag aaa gtc gat act aag aaa gaa gac    1824
Asp Ala Lys Lys Asp Asp Thr Lys Lys Val Asp Thr Lys Lys Glu Asp
        595                 600                 605 gct aaa aaa cca gaa gct aaa aaa cca gaa gct aag aaa gaa gaa gct    1872
Ala Lys Lys Pro Glu Ala Lys Lys Pro Glu Ala Lys Lys Glu Glu Ala
    610                 615                 620
```

FIG. 1C

```
aag aaa gaa gaa gct aag aaa gct gca act ctt cct aca act ggt gaa      1920
Lys Lys Glu Glu Ala Lys Lys Ala Ala Thr Leu Pro Thr Thr Gly Glu
625                 630                 635                 640 gga agc aac cca ttt ttc aca gct gct gcg ctt gca gta atg gct ggt      1968
Gly Ser Asn Pro Phe Phe Thr Ala Ala Ala Leu Ala Val Met Ala Gly
            645                 650                 655 gcg ggt gct ttg gca gtc gct tca aaa cgt aaa gaa gac taa              2010
Ala Gly Ala Leu Ala Val Ala Ser Lys Arg Lys Glu Asp
        660                 665                 670
```

FIG. 1D

IMMUNIZATION OF DAIRY CATTLE WITH MIG PROTEIN

CROSS-REFERENCE TO RELATED APPLICATION

This application is related to provisional patent application Ser. No. 60/211,016, filed Jun. 12, 2000, from which application priority is claimed under 35 USC §119(e)(1) and which application is incorporated herein by reference in its entirety.

TECHNICAL FIELD

The present invention relates generally to bacterial antigens and genes encoding the same. More particularly, the present invention pertains to the cloning, expression and characterization of the Mig Fc-receptor protein from several Streptococcus bacteria species, and the use of the same in vaccine compositions.

BACKGROUND

Mastitis is an infection of the mammary gland usually caused by bacteria or fungus. The inflammatory response following infection results in decreased milk yield as well as quality, and causes major annual economic losses to the dairy industry.

Among the bacterial species most commonly associated with mastitis are various species of the genus Streptococcus, including Streptococcus aureus, Streptococcus uberis (untypeable), Streptococcus agalactiae (Lancefield group B), Streptococcus dysgalactiae (Lancefield group C), Streptococcus zooepidemicus, and the Lancefield groups D, G, L and N streptococci. Some of those species are contagions (e.g. S. agalactiae), while others are considered environmental pathogens (e.g. S. dysgalactiae and S. uberis).

The environmental pathogen S. uberis is responsible for about 20% of all clinical cases of mastitis (Bramley, A. J. and Dodd, F. H. (1984) J. Dairy Res. 51:481–512; Bramley, A. J. (1987) Animal Health Nutrition 42:12–16; Watts, J. L. (1988) J. Dairy Sci. 71:1616–1624); it is the predominant organism isolated from mammary glands during the non-lactating period (Bramley, A. J. (1984) Br. Vet. J. 140:328–335; Bramley and Dodd (1984) J. Dairy Res. 51:481–512; Oliver, S. P. (1988) Am. J. Vet. Res. 49:1789–1793).

Mastitis resulting from infection with S. uberis is commonly subclinical, characterized by apparently normal milk with an increase in somatic cell counts due to the influx of leukocytes. The chemical composition of milk is changed due to suppression of secretion with the transfer of sodium chloride and bicarbonate from blood to milk, causing a shift of pH to a more alkaline level. S. uberis mastitis may also take the form of an acute clinical condition, with obvious signs of disease such as clots or discoloration of the milk and swelling or hardness of the mammary gland. Some cases of the clinical disease can be severe and pyrexia may be present. For a review of the clinical manifestations of S. uberis mastitis, see, Bramley (1991) Mastitis: physiology or pathology. p. 3–9. In C. Burvenich, G. Vandeputte-van Messom, and A. W. Hill (ed.), New insights into the pathogenesis of mastitis. Rijksuniversiteit Gent, Belgium; and Schalm et al. (1971) The mastitis complex-A brief summary. p. 1–3. In Bovine Mastitis. Lea & Febiger, Philadelphia.

Conventional antibacterial control methods such as teat dipping and antibiotic therapy are effective in the control of many types of contagious mastitis, but the environmental organisms typically found in all dairy barns are often resistant to such measures. Vaccination is therefore an attractive strategy to prevent infections of the mammary glands, and has been shown to be beneficial in the case of some contagious mastitis pathogens.

However, the literature is limited regarding vaccination studies with environmental pathogens such as S. dysgalactiae and S. uberis, and variable results have been observed. In some cases, immunization has resulted in increased sensitivity to the specific organism and in other cases strain-specific protection has been obtained.

For example, previous studies have shown that primary infection with S. uberis can considerably reduce the rate of infection following a second challenge with the same strain (Hill, A. W. (1988) Res. Vet. Sci. 44:386–387). Local vaccination with killed S. uberis protects the bovine mammary gland against intramammary challenge with the homologous strain (Finch et al. (1994) Infect. Immun. 62:3599–3603). Similarly, subcutaneous vaccination with live S. uberis has been shown to cause a dramatic modification of the pathogenesis of mastitis with the same strain (Hill et al. (1994) FEMS Immunol. Med. Microbiol. 8:109–118). Animals vaccinated in this way shed fewer bacteria in their milk and many quarters remain free of infection.

Nonetheless, vaccination with live or attenuated bacteria can pose risks to the recipient. Further, it is clear that conventional killed vaccines are in general largely ineffective against S. uberis and S. agalactiae, either due to lack of protective antigens on in vitro-grown cells or masking of these antigens by molecular mimicry.

The current lack of existing mastitis vaccines against S. agalactiae or the contagious streptococcus strains is due at least in part to a lack of knowledge regarding the virulence determinants and protective antigens produced by those organisms which are involved in invasion and protection of the mammary gland (Collins et al. (1988) J. Dairy Res. 55: 25–32; Leigh et al. (1990) Res. Vet. Sci. 49: 85–87; Marshall et al. (1986) J. Dairy Res. 53: 507–514).

S. dysgalactiae is known to bind several extracellular and plasma-derived proteins such as fibronectin, fibrinogen, collagen, alpha-II-macroglobulin, IgG, albumin and other compounds. The organism also produces hyaluronidase and fibrinolysin and is capable of adhering to and invading bovine mammary epithelial cells. However, the exact roles of the bacterial components responsible for these phenotypes in pathogenesis is not known.

Similarly, the pathogenesis of S. uberis infection is poorly understood. Furthermore, the influence of S. uberis virulence factors on host defense mechanisms and mammary gland physiology is not well defined. Known virulence factors associated with S. uberis include a hyaluronic acid capsule (Hill, A. W. (1988) Res. Vet. Sci. 45:400–404), hyaluronidase (Schaufuss et al. (1989) Zentralbl. Bakteriol. Ser. A 271:46–53), R-like protein (Groschup, M. H. and Timoney, J. F. (1993) Res. Vet. Sci. 54:124–126), and a cohemolysin, the CAMP factor, also known as UBERIS factor (Skalka, B. and Smola, J. (1981) Zentralbl. Bakteriol. Ser. A 249:190–194), R-like protein, plasminogen activator and CAMP factor. However, very little is known of their roles in pathogenicity.

The use of virulence determinants from Streptococcus as immunogenic agents has been proposed. For example, the CAMP factor of S. uberis has been shown to protect vertebrate subject from infection by that organism (Jiang, et al., U.S. Pat. No. 5,863,543).

The γ antigen of the group B Streptococci strain A909 (ATCC No. 27591) is a component of the c protein marker complex, which additionally comprises an α and β subunit (Boyle, U.S. Pat. No. 5,721,339). Subsets of serotype Ia, II, and virtually all serotype Ib cells of group B streptococci, have been reported to express components of the c protein. Use of the γ subunit as an immunogenic agent against infections by Lancefield Group B Streptococcus infection has been proposed. However, its use to prevent or treat bacterial infections in animals, including mastitis in cattle, has not been studied.

The group A streptococcal M protein is considered to be one of the major virulence factors of this organism by virtue of its ability to impede attack by human phagocytes (Lancefield, R. C. (1962) *J. Immunol.* 89:307–313). The bacteria persist in the infected tissue until antibodies are produced against the M molecule. Type-specific antibodies to the M protein are able to reverse the antiphagocytic effect of the molecule and allow efficient clearance of the invading organism.

M proteins are one of the key virulence factors of *Streptococcus pyogenes*, due to their involvement in mediating resistance to phagocytosis (Kehoe, M. A. (1991) *Vaccine* 9:797–806) and their ability to induce potentially harmful host immune responses via their superantigenicity and their capacity to induce host-cross-reactive antibody responses (Bisno, A. L. (1991) *New Engl. J. Med.* 325:783–793; Froude et al. (1989) *Curr. Top. Microbiol. Immunol.* 145:5–26; Stollerman, G. H. (1991) *Clin. Immunol. Immunopathol.* 61:131–142).

However, obstacles exist to using intact M proteins as vaccines. The protein's opsonic epitopes are extremely type-specific, resulting in narrow, type-specific protection. Further, some M proteins appear to contain epitopes that cross react with tissues of the immunized subject, causing a harmful autoimmune response (See e.g. Dale, J. G. and Beachey, E. H. (1982) *J. Exp. Med.* 156:1165–1176; Dale, J. B. and Beachey, E. H. (1985) J. Exp. Med. 161:113–122; Baird, R. W., Bronze, M. S., Draus, W., Hill, H. R., Veasey, L. G. and Dale, J. B. (1991) *J. Immun.* 146:3132–3137; Bronze, M. S. and Dale, J. B. (1993) *J. Immun* 151:2820–2828; Cunningham, M. W. and Russell, S. M. (1983) *Infect. Immun.* 42:531–538).

Chimeric proteins containing three different fibronectin binding domains (FNBDs) derived from fibronectin binding proteins of *S. dysgalactiae* and *Staphylococcus aureus* have been expressed on the surface of *Staph. Carnosus* cells. In the case of one of these proteins, intranasal immunizations with live recombinant *Staph. Carnosus* cells expressing the chimeric protein on their surface resulted in an improved antibody response to a model immunogen present within the chimeric surface protein (Liljeqvist, S. et al. (1999) *FEBS Letters* 446:299–304).

Bacterial Fc receptors (surface moieties that bind to immunoglobulin molecules through a non-immune mechanism, i.e., to the Fc portion of the antibody) are a class of binding proteins further categorized by their reactivity with different classes and subclasses of mammalian immunoglobulins. The type I receptor (also known as Protein A), the most extensively studied and characterized, has been isolated from *Staphylococcus aureus*, and binds to IgG types 1,2 and 4; this receptor type further exhibits cross-reactivity with IgA and IgM. The type II Fc receptor, found on a few Lancefield Group A streptococci, and the type III receptor (also known as Protein G), found on the majority of human group C and group G strains of streptococcus, have been reported to react with all four types of IgG. In the case of the type III receptor, binding to IgG is highly specific; the protein does not cross-react with IgA or IgM. The type IV receptor is found in certain bovine group G streptococci, and the type V receptor is found on certain strains of *Streptococcus zooepidemicus*. The type VI Fc receptor has been isolated from *S. zooepidemicus* strains S212 and RSS-212, and binds rat IgG with high affinity, i.e., 100 times that of Protein A binding, and 30 to 40 times as great as Protein G binding. (Boyle, et al., U.S. Pat. No. 4,977,082). For a discussion of Fc receptors, see Langone (1982) *Adv. Immunol.* 32:167 and Myhre et al. (1984) *Basic Concepts of Streptococci and Streptococcal Diseases* (Holm & Christensen, eds.) Redbook Ltd., Chertsey, Surrey, England.

Utility for Fc binding proteins have to date been limited to antibody detection and purification. With respect to clinical applications, a method of extracorporeal blood treatment of autoimmune disease which employs Fc binding proteins to remove antigen-antibody complexes has been proposed (see e.g. Fahnestock, U.S. Pat. No. 4,954,618). However, their use in vaccine compositions has not previously been described nor suggested.

Until now, the protective capability of the *S. dysgalactiae* Mig protein against mastitis has not been studied, nor has the *S. dysgalactiae* Mig protein been isolated or characterized.

SUMMARY OF THE INVENTION

Accordingly, the present invention provides Fc receptor proteins and uses therefor. In one embodiment, the invention is directed to a vaccine composition comprising a pharmaceutically acceptable vehicle and an Fc receptor protein. In certain embodiments, the Fc receptor protein is selected from the group consisting of:

(a) a *Streptococcus dysgalactiae* Mig protein comprising the amino acid sequence shown at amino acid positions 1 to 669, inclusive, of FIGS. 1A–1D (SEQ ID NO:4);

(b) an Fc receptor protein having at least about 70% sequence identity to (a); and (c) immunogenic fragments of (a) and (b), said fragments comprising at least about 5 amino acids.

In some embodiments, the vaccine composition comprises and adjuvant.

In yet further embodiments, the invention is directed to a method of producing a vaccine composition. The method comprises the steps of (a) providing an Fc receptor protein or an immunogenic fragment thereof, the fragment comprising at least about 5 amino acids, and (b) combining said protein with a pharmaceutically acceptable vehicle.

In another embodiment, the invention is directed to a method of treating or preventing a bacterial infection in a vertebrate subject. The method comprises administering to the subject a therapeutically effective amount of a vaccine composition as described above.

In certain embodiments the bacterial infection is a streptococcal infection. Additionally, the bacterial infection may cause mastitis.

In yet another embodiment, the invention is directed to a method of treating or preventing a bacterial infection in a vertebrate subject comprising administering to the subject a therapeutically effective amount of a polynucleotide that comprises a coding sequence for an Fc receptor protein.

In certain embodiments, the bacterial infection is a streptococcal infection and may cause mastitis.

These and other embodiments of the present invention will readily occur to those of ordinary skill in the art in view of the disclosure herein.

BRIEF DESCRIPTION OF THE FIGURES

FIGS. 1A–1D depict the polynucleotide sequence encoding the *Streptococcus dysgalactiae* Mig protein, and the amino acid sequence deduced therefrom (SEQ ID NO:3 and SEQ ID NO:4, respectively).

DETAILED DESCRIPTION OF THE INVENTION

Figure 2:
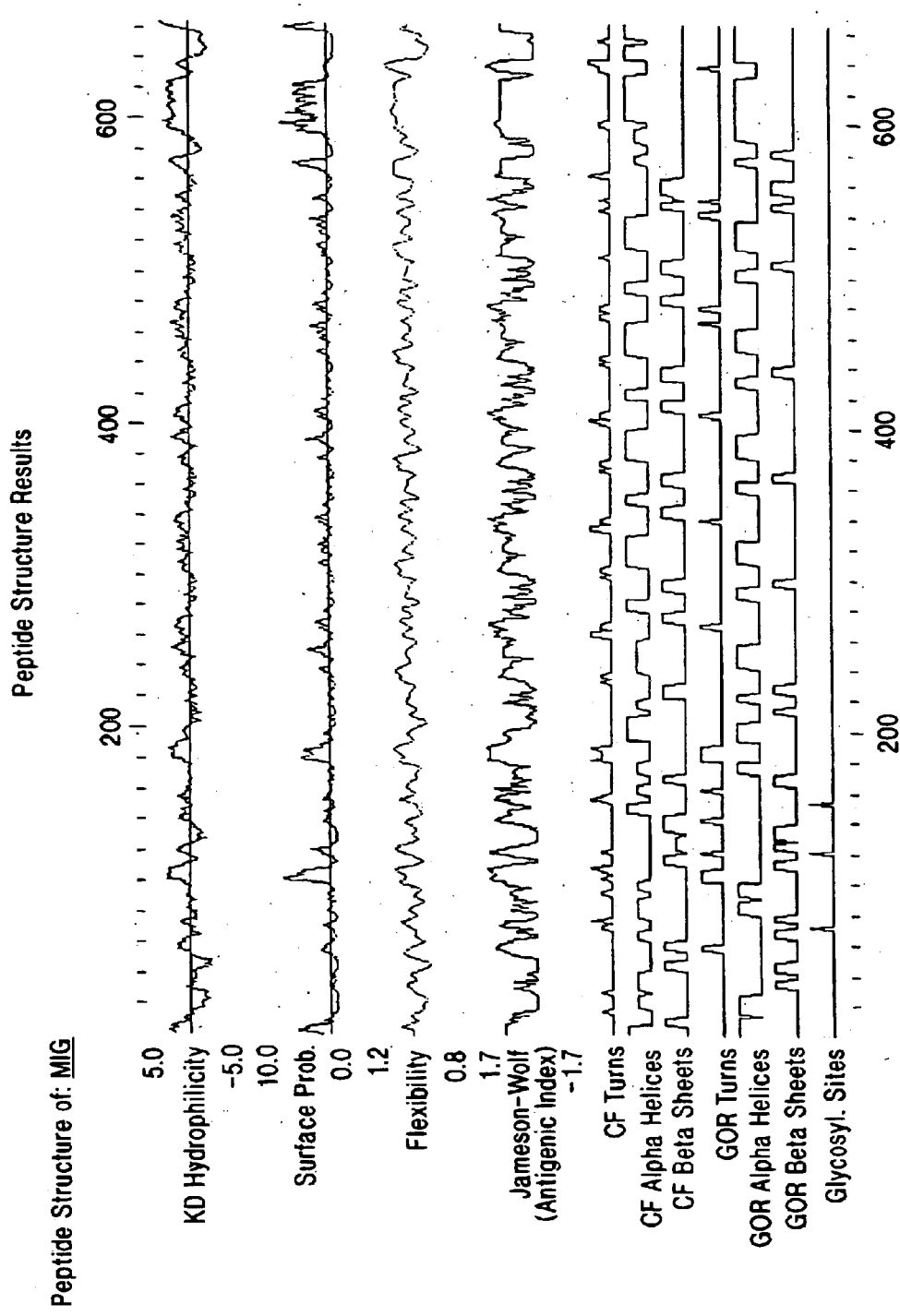
FIG. 2 presents the following results for peptide structure analysis of the *S. dysgalactiae* Mig protein a: Kyle-Doolittle Hydropathy plot ("KD Hydrophilicity"), averaged over a window of 7; an Emini surface probability plot ("Surface Prob."); a Karplus-Schulz chain flexibility plot ("Flexibility"); a Jameson-Wolf antigenic index plot, and both Chou-Fasman and Garnier-Osguthorpe-Robson secondary structure plots ("CF Alpha Helices" and "CF Beta Sheets"; and "GOR Turns," "GOR Alpha Helices," "GOR Beta Sheets," and "Glycosylation Sites," respectively).

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual*, Vols. I, II and III, Second Edition (1989); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a *Streptococcus dysgalactiae* Fc binding protein" includes a mixture of two or more such proteins, and the like.

The terms "Fc receptor protein" and "Fc binding protein," used interchangeably herein, denote a bacterial protein capable of binding to immunoglobulin molecules at a site other than the antigen recognition site, including without limitation the Fc region of an immunoglobulin molecule.

The terms "Mig protein" and "Mig Fc receptor protein" and "Mig Fc binding protein" (used interchangeably herein) or a nucleotide sequence encoding the same, intends a protein or a nucleotide sequence, respectively, which is derived from a Mig gene found in a variety of bacterial species, including, without limitation, certain strains of group A streptococci. The nucleotide sequence of a representative *Streptococcus Mig* gene from *S. dysgalactiae* (SEQ ID NO:3), and the corresponding amino acid sequence encoded by that gene (SEQ ID NO:4), is depicted in FIGS. 1A–1D. However, a Mig protein as defined herein is not limited to the depicted sequences as subtypes of each of these Streptococcus species are known and variations in Mig proteins will occur between them.

A representative Mig gene derived from *S. dysgalactiae* is found in the plasmid pAA505Mig.

Furthermore, the derived protein or nucleotide sequences need not be physically derived from the gene described above, but may be generated in any manner, including for example, chemical synthesis, isolation (e.g., from *S. dysgalactiae*) or by recombinant production, based on the information provided herein. Additionally, the term intends proteins having amino acid sequences substantially homologous (as defined below) to contiguous amino acid sequences encoded by the genes, which display immunological and/or plasmin-binding activity.

Thus, the terms intend full-length, as well as immunogenic, truncated and partial sequences, and active analogs and precursor forms of the proteins. Also included in the term are nucleotide fragments of the gene that include at least about 8 contiguous base pairs, more preferably at least about 10–20 contiguous base pairs, and most preferably at least about 25 to 50, or more, contiguous base pairs of the gene, or any integers between these values. Such fragments are useful as probes and in diagnostic methods, discussed more fully below.

The terms also include those forms possessing, as well as lacking, a signal sequence, if such is present, as well as the nucleic acid sequences coding therefore. Additionally, the term intends forms of the Mig proteins which lack a membrane anchor region, and nucleic acid sequences encoding proteins with such deletions. Such deletions may be desirable in systems that do not provide for secretion of the protein. Furthermore, the Fc receptor-binding domains of the proteins, may or may not be present. Thus, for example, if the Mig Fc binding protein will be used to purify immunoglobulin, the Fc binding domain will generally be retained. If the protein is to be used in vaccine compositions, immunogenic epitopes which may or may not include the Fc receptor binding domain, will be present.

The terms also include proteins in neutral form or in the form of basic or acid addition salts depending on the mode of preparation. Such acid addition salts may involve free amino groups and basic salts may be formed with free carboxyls. Pharmaceutically acceptable basic and acid addition salts are discussed further below. In addition, the proteins may be modified by combination with other biological materials such as lipids (both those occurring naturally with the molecule or other lipids that do not destroy immunological activity) and saccharides, or by side chain modification, such as acetylation of amino groups, phosphorylation of hydroxyl side chains, oxidation of sulfhydryl groups, glycosylation of amino acid residues, as well as other modifications of the encoded primary sequence.

The term therefore intends deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule, but possessing minor amino acid substitutions that do not substantially affect the immunogenicity and/or plasmin-binding affinity of the protein, are therefore within the definition of the reference polypeptide.

For example, the polypeptide of interest may include up to about 5–10 conservative or non-conservative amino acid substitutions, or even up to about 15–25 or 20–50 conservative or non-conservative amino acid substitutions, or any integer between these values, so long as the desired function of the molecule remains intact.

Similarly, substitutions occurring in the transmembrane binding domain, if present, and the signal sequence, if present, normally will not affect immunogenicity. One of skill in the art may readily determine other regions of the molecule of interest that can tolerate change by reference to the peptide structure plots shown in FIG. 2 and FIG. 3 herein.

The term "streptococcal Mig protein" intends a Mig Fc binding protein, as defined above, derived from a streptococcal species that produces the same, including, but not limited to S. dysgalactiae. For example, a "S. dysgalactiae Mig protein" is a Fc binding protein as defined above, derived from S. dysgalactiae.

"Wild type" or "native" proteins or polypeptides refer to proteins or polypeptides isolated from the source in which the proteins naturally occur. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

An "isolated" protein or polypeptide is a protein or polypeptide molecule separate and discrete from the whole organism with which the molecule is found in nature; or a protein or polypeptide devoid, in whole or part, of sequences normally associated with it in nature; or a sequence, as it exists in nature, but having heterologous sequences (as defined below) in association therewith.

The term "functionally equivalent" intends that the amino acid sequence of a Mig Fc binding protein is one that will elicit a substantially equivalent or enhanced immunological response, as defined above, as compared to the response elicited by a Fc binding protein having identity with the reference Fc binding protein, or an immunogenic portion thereof.

The term "epitope" refers to the site on an antigen or hapten to which specific B cells and/or T cells respond. The term is also used interchangeably with "antigenic determinant" or "antigenic determinant site." Antibodies that recognize the same epitope can be identified in a simple immunoassay showing the ability of one antibody to block the binding of another antibody to a target antigen.

The terms "immunogenic" protein or polypeptide refer to an amino acid sequence which elicits an immunological response as described below. An "immunogenic" protein or polypeptide, as used herein, includes the full-length sequence of the Fc receptor protein in question, with or without the signal sequence, membrane anchor domain and/or Fc binding domain, analogs thereof, or immunogenic fragments thereof.

By "immunogenic fragment" is meant a fragment of an Fc receptor protein which includes one or more epitopes and thus elicits the immunological response described below. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1986) *Molec. Immunol.* 23:709–715, all incorporated herein by reference in their entireties.

Figure 3:
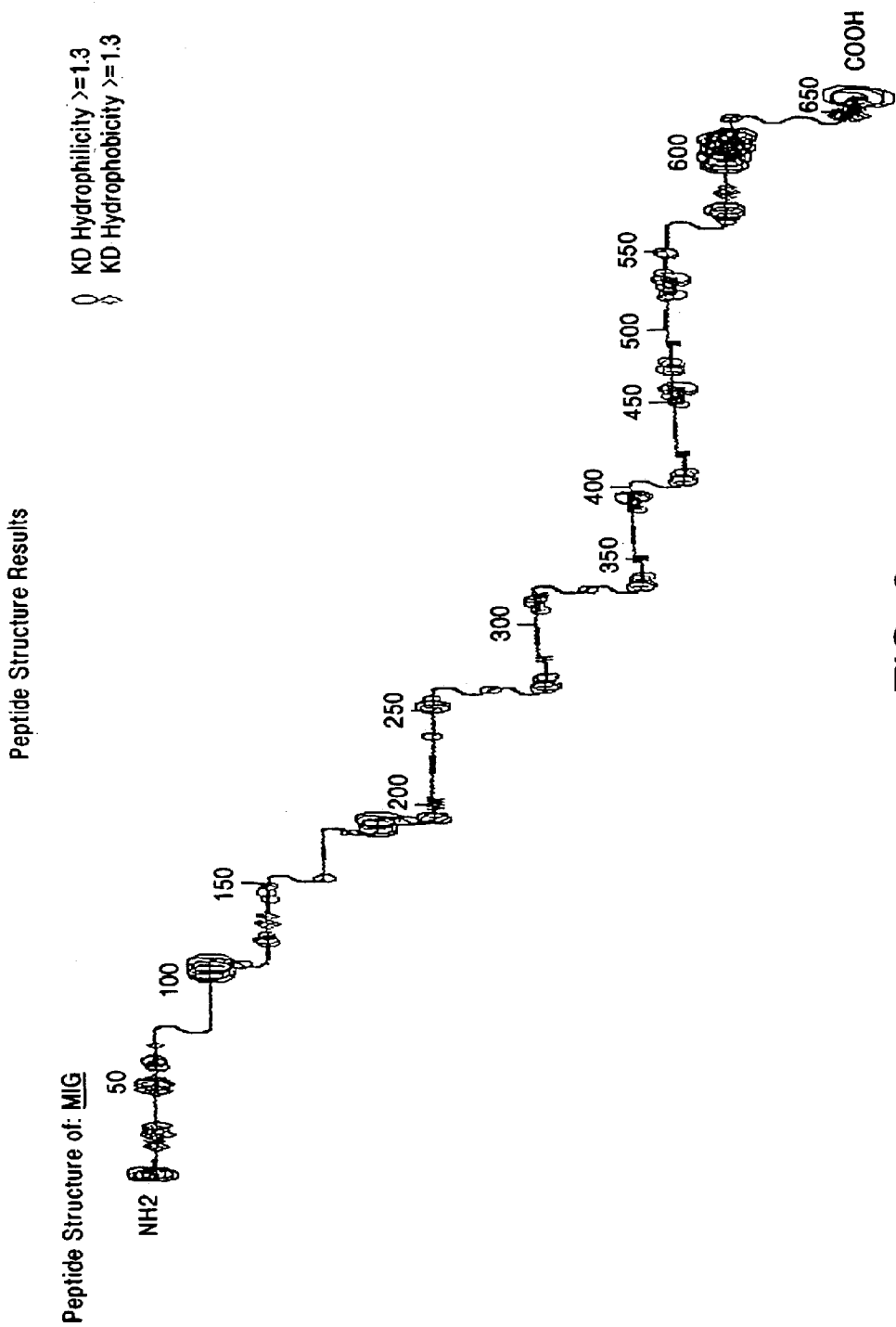
FIG. 3 is a Chou-Fasman secondary structure plot for the *S. dysgalactiae* Mig protein.

Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824–3828 for determining antigenicity profiles, and the Kyte-Doolittle technique, Kyte et al., *J. Mol. Biol.* (1982) 157:105–132 for hydropathy plots. FIGS. 2 and 3 herein depict Kyte-Doolittle profiles for representative proteins encompassed by the invention.

Immunogenic fragments, for purposes of the present invention, will usually include at least about 3 amino acids, preferably at least about 5 amino acids, more preferably at least about 10–15 amino acids, and most preferably 25 or more amino acids, of the parent Mig Fc receptor protein molecule. There is no critical upper limit to the length of the fragment, which may comprise nearly the full-length of the protein sequence, or even a fusion protein comprising two or more epitopes of Mig.

An "immunogenic composition" is a composition that comprises an antigenic molecule where administration of the composition to a subject results in the development in the subject of a humoral and/or a cellular immune response to the antigenic molecule of interest.

By "subunit vaccine composition" is meant a composition containing at least one immunogenic polypeptide, but not all antigens, derived from or homologous to an antigen from a pathogen of interest. Such a composition is substantially free of intact pathogen cells or particles, or the lysate of such cells or particles. Thus, a "subunit vaccine composition" is prepared from at least partially purified (preferably substantially purified) immunogenic polypeptides from the pathogen, or recombinant analogs thereof. A subunit vaccine composition can comprise the subunit antigen or antigens of interest substantially free of other antigens or polypeptides from the pathogen.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display either a therapeutic or protective immunological response such that resistance of the mammary gland to new infection will be enhanced and/or the clinical severity of the disease reduced. Such protection will be demonstrated by either a reduction or lack of symptoms normally displayed by an infected host and/or a quicker recovery time.

By "nucleic acid immunization" is meant the introduction of a nucleic acid molecule encoding one or more selected antigens into a host cell, for the in vivo expression of an antigen, antigens, an epitope, or epitopes. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

The term "treatment" as used herein refers to either (1) the prevention of infection or reinfection (prophylaxis), or (2) the reduction or elimination of symptoms of the disease of interest (therapy).

By "mastitis" is meant an inflammation of the mammary gland in mammals, including in cows, ewes, goats, sows, mares, and the like, caused by the presence of S. uberis. The infection manifests itself by the infiltration of phagocytic cells in the gland. Generally, 4 clinical types of mastitis are recognized: (1) peracute, associated with swelling, heat, pain, and abnormal secretion in the gland and accompanied by fever and other signs of systemic disturbance, such as marked depression, rapid weak pulse, sunken eyes, weakness and complete anorexia; (2) acute, with changes in the gland similar to those above but where fever, anorexia and depression are slight to moderate; (3) subacute, where no systemic changes are displayed and the changes in the gland and its secretion are less marked: and (4) subclinical, where the inflammatory reaction is detectable only by standard tests for mastitis.

Standard tests for the detection of mastitis include but are not limited to, the California Mastitis Test, the Wisconsin Mastitis Test, the Nagase test, the electronic cell count and somatic cell counts used to detect a persistently high white blood cell content in milk. In general, a somatic cell count of about 300,000 to about 500,000 cells per ml or higher, in milk will indicate the presence of infection. Thus, a vaccine is considered effective in the treatment and/or prevention of mastitis when, for example, the somatic cell count in milk is retained below about 500,000 cells per ml. For a discussion of mastitis and the diagnosis thereof, see, e.g., *The Merck Veterinary Manual: A Handbook of Diagnosis, Therapy, and Disease Prevention and Control for the Veterinarian*, Merck and Co., Rahway, N.J., 1991.

By the terms "vertebrate," "subject," and "vertebrate subject" are meant any member of the subphylum Chordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds; and fish. The term does not denote a particular age. Thus, both adult and newborn animals, as well as fetuses, are intended to be covered.

A "nucleic acid" molecule can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith. The term "isolated" in the context of a polynucleotide intends that the polynucleotide is isolated from the chromosome with which it is normally associated, and is isolated from the complete genomic sequence in which it normally occurs.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "coding sequence" or a "nucleotide sequence encoding" a particular protein, is a nucleotide sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence. A "complementary" sequence is one in which the nitrogenous base at a given nucleotide position is the complement of the nitrogenous base appearing at the same position in the reference sequence. To illustrate, the complement of adenosine is tyrosine, and vice versa; similarly, cytosine is complementary to guanine, and vice versa; hence, the complement of the reference sequence 5'-ATGCTGA-3' would be 5'-TACGACT-3'.

A "wild-type" or "native" sequence, as used herein, refers to polypeptide encoding sequences that are essentially as they are found in nature, e.g., the S. dysgalactiae Mig protein coding sequences depicted in FIGS. 1A–1D (SEQ ID NO:4).

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

"Homology" refers to the percent identity between two polynucleotide or two polypeptide moieties. Two DNA, or two polypeptide sequences are "substantially homologous" to each other when the sequences exhibit at least about 80%–85%, preferably at least about 90%, and most preferably at least about 95%–98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman (1981) *Advances in Appl. Math.* 2:482–489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.nih.gov/BLAST/.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A "vector" is a replicon, such as a plasmid, phage, or cosmid, to which another DNA segment may be attached so as to bring about the replication of he attached segment. A vector is capable of transferring gene sequences to target cells (e.g., bacterial plasmid vectors, viral vectors, non-viral vectors, particulate carriers, and liposomes).

Typically, the terms "vector construct," "expression vector," "gene expression vector," "gene delivery vector," "gene transfer vector," and "expression cassette" all refer to an assembly which is capable of directing the expression of a sequence or gene of interest. Thus, the terms include cloning and expression vehicles, as well as viral vectors.

These assemblies include a promoter which is operably linked to the sequences or gene(s) of interest. Other control elements may be present as well. The expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

DNA "control elements" refers collectively to transcription promoters, transcription enhancer elements, transcription termination sequences, polyadenylation sequences (located 3' to the translation stop codon), sequences for optimization of initiation of translation (located 5' to the coding sequence), translation termination sequences, upstream regulatory domains, ribosome binding sites and the like, which collectively provide for the transcription and translation of a coding sequence in a host cell. See e.g., McCaughan et al. (1995) *PNAS USA* 92:5431–5435; Kochetov et al (1998) *FEBS Letts.* 440:351–355. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence. Similarly, "control elements compatible with expression in a subject" are those which are capable of effecting the expression of the coding sequence in that subject.

A control element, such as a promoter, "directs the transcription" of a coding sequence in a cell when RNA polymerase will bind the promoter and transcribe the coding sequence into mRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescors, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH and α-β-galactosidase.

2. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the discovery that the Mig Fc binding protein isolated from *S. dysgalactiae* is capable of eliciting an immune response in a vertebrate subject. In particular, the gene for the Mig protein in *S.*

*dysgalactiae* has been isolated, sequenced and characterized, and the amino acid sequence encoded by the gene has been deduced therefrom. The complete DNA sequence for the *S. dysgalactiae* mig gene (SEQ ID NO:3) and the corresponding amino acid sequence (SEQ ID NO:4) are shown in FIGS. 1A–1D.

As described in the examples, the full-length *S. dysgalactiae* mig gene, depicted at nucleotide positions 1–2,010 inclusive, of FIGS. 1A–1D, encodes the full-length *S. dysgalactiae* Mig protein of 669 amino acids, which includes a first 24 amino acid transmembrane region (residues 15 and 39) and a second 18 amino acid transmembrane region of 18 amino acids (residues 646–664). Transmembrane regions were determined using the TMpred program, which predicts membrane-spanning regions and their orientation. The program uses an algorithm based on the statistical analysis of TMbase, a database of naturally occurring transmembrane proteins, using a combination of several weight matrices for scoring. See Hofiann, K., & Stoffel, W. (1993) *Biol. Chem.* 347:166.

*S. dysgalactiae* Mig has a predicted molecular weight of about 73 kDa. (calculated using the Peptide Sort program of the GCG Wisconsin Package, version 10, provided by the SeqWeb sequence analysis package, version 1.1 of the Canadian Bioinformatics Resource). The full-length sequence includes a signal peptide.

FIG. 2 plots the following structural analyses results for the Mig protein of the present invention: Kyte-Doolittle hydrophathy, averaged over a window of 7; surface probability according to Emini; chain flexibility according to Karplus-Schulz; antigenicity index according to Jameson-Wolf; secondary structure according to Garnier-Osguthorpe-Robson; secondary structure according to Chou-Fasman; and predicted glycosylation sites. FIG. 3 plots secondary structure according to Chou-Fasman for the Mig protein of the present invention. One of skill in the art can readily use the information presented in FIGS. 2 and 3 to determine immunogenic regions in the protein for use in vaccine compositions.

Mig Fc receptor proteins, including without limitation the *S. dysgalactiae* Mig protein, immunogenic fragments thereof or chimeric proteins including the same, can be provided in subunit vaccine compositions. In addition to use in vaccine compositions, the proteins or antibodies thereto can be used as diagnostic reagents to detect the presence of infection in a vertebrate subject. Similarly, the genes encoding the proteins can be cloned and used to design probes to detect and isolate homologous genes in other bacterial strains. For example, fragments comprising at least about 15–20 nucleotides, more preferably at least about 20–50 nucleotides, and most preferably about 60–100 nucleotides, or any integer between these values, will find use in these embodiments.

The vaccine compositions of the present invention can be used to treat or prevent a wide variety of bacterial infections in vertebrate subjects. For example, vaccine compositions including, without limitation, the Mig Fc receptor protein from *S. dysgalactiae*, can be used to treat streptococcal infections in vertebrate subjects that are caused by this or other species. In particular, *S. uberis, S. agalactiae*, and *S. dysgalactiae* are common bacterial pathogens associated with mastitis in bovine, equine, ovine and goat species. Additionally, group B streptococci, such as *S. agalactiae*, are known to cause numerous other infections in vertebrates, including septicemia, meningitis, bacteremia, impetigo, arthritis, urinary tract infections, abscesses, spontaneous abortion etc. Hence, vaccine compositions containing the Mig Fc receptor protein will find use in treating and/or preventing a wide variety of streptococcal infections.

Similarly, Fc binding proteins derived from other bacterial genera such as Staphylococcus will find use for treating bacterial infections caused by species belonging to those genera. Thus, it is readily apparent that Fc binding proteins from a variety of bacterial species can be used to treat and/or prevent a wide variety of bacterial infections in numerous animal species.

The streptococcal Fc binding proteins of the present invention, including without limitation to the Mig Fc binding protein, can be used in vaccine compositions either alone or in combination with other bacterial, fungal, viral or protozoal antigens. These antigens can be provided separately or even as fusion proteins comprising one or more epitopes of an Fc binding protein fused to one or more of these antigens. For example, other immunogenic proteins from *S. uberis*, such as the CAMP factor, hyaluronic acid capsule, hyaluronidase, R-like protein and plasminogen activator, can be administered with the Mig protein. Additionally, immunogenic proteins from other organisms involved in mastitis, such as from the genera Staphylococcus, Corynebacterium, Pseudomonas, Nocardia, Clostridium, Mycobacterium, Mycoplasma, Pasteurella, Prototheca, other streptococci, coliform bacteria, as well as yeast, can be administered along with the Fc binding proteins described herein to provide a broad spectrum of protection. Thus, for example, immunogenic proteins from *Staphylococcus aureus, Str. agalactiae, Str. dysgalactiae, Str. zooepidemicus, Corynebacterium pyogenes, Pseudomonas aeruginosa, Nocardia asteroides, Clostridium perfringens, Escherichia coli, Enterobacter aerogenes* and *Klebsiella spp.* can be provided along with the Fc binding proteins of the present invention.

Additionally, Fc proteins from different streptococcal species may be used together in the vaccine compositions of the present invention. In this embodiment, the multiple Fc proteins may be provided either as fusion proteins or as discrete antigens in the same or different vaccine compositions.

Production of Fc Binding Proteins

The above-described Fc binding proteins and active fragments, analogs and chimeric proteins derived from the same, can be produced by variety of methods. Specifically, Fc binding proteins can be isolated directly from bacteria which express the same. This is generally accomplished by first preparing a crude extract which lacks cellular components and several extraneous proteins. The desired proteins can then be further purified from the cell lysate fraction by, e.g., column chromatography, HPLC, immunoadsorbent techniques or other conventional methods well known in the art.

More particularly, techniques for isolating Fc binding proteins have been described. For example, the methods of Reis, et al. have been used to isolate a functionally homogeneous Fc receptor having the properties of a type-III receptor (Reis et al., (1984) *J. Immunol.* 132:3091).

Alternatively, the proteins can be recombinantly produced as described herein. As explained above, these recombinant products can take the form of partial protein sequences, full-length sequences, precursor forms that include signal sequences, mature forms without signals, or even fusion proteins (e.g., with an appropriate leader for the recombinant host, or with another subunit antigen sequence for Streptococcus or another pathogen).

In one embodiment of the present invention, the *S. dysgalactiae* Mig protein is purified from a cell lysate fraction using affinity chromatography after recombinantly producing the protein. See Example 1A–D, infra.

Gene libraries can be constructed and the resulting clones used to transform an appropriate host cell. Colonies can be pooled and screened for clones having Fc receptor binding activity, i.e., for clones capable of binding IgG.

Alternatively, once the amino acid sequences are determined, oligonucleotide probes which contain the codons for a portion of the determined amino acid sequences can be prepared and used to screen genomic or cDNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. II, supra; *Nucleic Acid Hybridization*, supra; *Oligonucleotide Synthesis*, supra; Sambrook et al., supra. Once a clone from the screened library has been identified by positive hybridization, it can be confirmed by restriction enzyme analysis and DNA sequencing that the particular library insert contains a Fc binding protein gene or a homolog thereof. The genes can then be further isolated using standard techniques and, if desired, PCR approaches or restriction enzymes employed to delete portions of the full-length sequence.

Similarly, genes can be isolated directly from bacteria using known techniques, such as phenol extraction and the sequence further manipulated to produce any desired alterations. See, e.g., Sambrook et al., supra, for a description of techniques used to obtain and isolate DNA.

Alternatively, DNA sequences encoding the proteins of interest can be prepared synthetically rather than cloned. The DNA sequences can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage γ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, Sambrook et al., supra; *DNA Cloning*, supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. If a signal sequence is included, it can either be the native, homologous sequence, or a heterologous sequence. For example, the signal sequence for the *S. dysgalactiae* Mig protein (amino acid residue 1 to 39, inclusive) can be used for secretion thereof, as can a number of other signal sequences, well known in the art. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the Fc binding protein. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., *supra; DNA Cloning, supra; Nucleic Acid Hybridization, supra.*

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis*, and Streptococcus spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni.*

Depending on the expression system and host selected, the proteins of the present invention are produced by culturing host cells transformed by an expression vector described above under conditions whereby the protein of interest is expressed. The protein is then isolated from the host cells and purified. If the expression system secretes the protein into the growth media, the protein can be purified directly from the media. If the protein is not secreted, it is isolated from cell lysates. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art.

See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis. Chemical synthesis of peptides may be preferable if a small fragment of the antigen in question is capable of raising an immunological response in the subject of interest.

The Fc binding proteins of the present invention, or their fragments, can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. See, e.g., Jurgens et al. (1985) *J. Chrom.* 348:363–370. If serum containing polyclonal antibodies is used, the polyclonal antibodies can be purified by immunoaffinity chromatography, using known procedures.

Monoclonal antibodies to the Mig protein and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the Mig protein, or fragments thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies can also be used for passive immunization or can be combined with subunit vaccine preparations to enhance the immune response. Polyclonal and monoclonal antibodies are also useful for diagnostic purposes.

Vaccine Formulations and Administration

The Fc binding proteins of the present invention can be formulated into vaccine compositions, either alone or in combination with other antigens, for use in immunizing subjects as described below. Methods of preparing such formulations are described in, e.g., *Remington's Pharmaceutical Sciences*, Mack Publishing Company, Easton, Pa., 18 Edition, 1990. Typically, the vaccines of the present invention are prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the vaccine may also be added to the formulation. Adjuvants may include for example, muramyl dipeptides, avridine, aluminum hydroxide, dimethyldioctadecyl ammonium bromide (DDA), oils, oil-in-water emulsions, saponins, cytokines, and other substances known in the art.

The Mig protein may be linked to a carrier in order to increase the immunogenicity thereof. Suitable carriers include large, slowly metabolized macro-molecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

The Fc binding proteins of the present invention may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl) propionate. Suitable carriers may also be modified to incorporate spacer arms (such as hexamethylene diamine or other bifunctional molecules of similar size) for attachment of peptides.

Other suitable carriers for the Fc binding proteins of the present invention include VP6 polypeptides of rotaviruses, or functional fragments thereof, as disclosed in U.S. Pat. No. 5,071,651, incorporated herein by reference. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

Furthermore, the Fc binding proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Vaccine formulations will contain a "therapeutically effective amount" of the active ingredient, that is, an amount capable of eliciting an immune response in a subject to which the composition is administered. In the treatment and prevention of mastitis, for example, a "therapeutically effective amount" would preferably be an amount that enhances resistance of the mammary gland to new infection and/or reduces the clinical severity of the disease. Such protection will be demonstrated by either a reduction or lack of symptoms normally displayed by an infected host, a quicker recovery time and/or a lowered somatic cell count in milk from the infected quarter. For example, the ability of the composition to retain or bring the somatic cell count (SCC) in milk below about 500,000 cells per ml, the threshold value set by the International Dairy Federation, above which, animals are considered to have clinical mastitis, will be indicative of a therapeutic effect.

The exact amount is readily determined by one skilled in the art using standard tests. The Fc binding protein concentration will typically range from about 1% to about 95% (w/w) of the composition, or even higher or lower if appropriate. With the present vaccine formulations, 5 to 500 µg of active ingredient per ml of injected solution should be adequate to raise an immunological response when a dose of 1 to 3 ml per animal is administered.

To immunize a subject, the vaccine is generally administered parenterally, usually by intramuscular injection. Other modes of administration, however, such as subcutaneous, intraperitoneal and intravenous injection, are also acceptable. The quantity to be administered depends on the animal to be treated, the capacity of the animal's immune system to synthesize antibodies, and the degree of protection desired. Effective dosages can be readily established by one of ordinary skill in the art through routine trials establishing dose response curves. The subject is immunized by administration of the vaccine in at least one dose, and preferably two doses. Moreover, the animal may be administered as many doses as is required to maintain a state of immunity to infection.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The Fc binding proteins can also be delivered using implanted mini-pumps, well known in the art.

The Fc binding proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK recombinant can be selected by culturing the cells in the presence of 5-bromodeoxyuridine and picking viral plaques resistant thereto.

An alternative route of administration involves gene therapy or nucleic acid immunization. Thus, nucleotide sequences (and accompanying regulatory elements) encoding the subject Fc binding proteins can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see International Publication No. WO/90/11092; and Wolff et al. (1990) *Science* 247:1465–1468). Liposome-mediated gene transfer can also be accomplished using known methods. See, e.g., Hazinski et al. (1991) *Am. J. Respir. Cell Mol. Biol.* 4:206–209; Brigham et al. (1989) *Am. J Med. Sci.* 298:278–281; Canonico et al. (1991) *Clin. Res.* 39:219A; and Nabel et al. (1990) *Science* 249:1285–1288. Targeting agents, such as antibodies directed against surface antigens expressed on specific cell types, can be covalently conjugated to the liposomal surface so that the nucleic acid can be delivered to specific tissues and cells susceptible to infection.

Deposits of Strains Useful in Practicing the Invention

A deposit of biologically pure cultures of the following strains was made with the American Type Culture Collection, 10801 University Boulevard, Manassas. The accession number indicated was assigned after successful viability testing, and the requisite fees were paid. made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit. The organisms will be made available by the ATCC under the terms of the Budapest Treaty, which assures permanent and unrestricted availability of the progeny to one determined by the U.S. Commissioner of Patents and Trademarks to be entitled thereto according to 35 U.S.C. §122 and the Commissioner's rules pursuant thereto (including 37 C.F.R. §1.12 with particular reference to 886 OG 638). Upon the granting of a patent, all restrictions on the availability to the public of the deposited cultures will be irrevocably removed.

These deposits are provided merely as convenience to those of skill in the art, and are not an admission that a deposit is required under 35 U.S.C. §112. The nucleic acid sequences of these genes, as well as the amino acid sequences of the molecules encoded thereby, are incorporated herein by reference and are controlling in the event of any conflict with the description herein.

| Bacterial Strain | Plasmid | Gene | Deposit Date | ATCC No. |
|---|---|---|---|---|
| DH5α | pAA505Mig | *S. dysgalactiae* mig gene | May 31, 2000 | PTA-1977 |

Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Unless indicated otherwise, parts are parts by weight, molecular weight is weight average molecular weight, temperature is in degrees Centigrade, and pressure is at or near atmospheric.

Materials and Methods

Enzymes were purchased from commercial sources, and used according to the manufacturers' directions.

In the isolation of DNA fragments, except where noted, all DNA manipulations were done according to standard procedures. See, Sambrook et al., supra. Restriction enzymes, $T_4$ DNA ligase, *E. coli*, DNA polymerase I, Klenow fragment, and other biological reagents can be purchased from commercial suppliers and used according to the manufacturers' directions. Double stranded DNA fragments were separated on agarose gels.

EXAMPLE 1

Preparation Amplification, Sequencing, Expression, Purification and Characterization of the *S. dvsgalactiae* Mig Fc Receptor Protein A. Preparation of *S. dvsgalactiae* Chromosomal DNA A clinical *S. dysgalactiae* isolate from a case of bovine mastitis (ATCC Accession No. 43078) was obtained from the American Type Culture Collection (10801 University Boulevard, Manassas, Va. 20110–2209), and was used as a source of DNA. The organism was routinely grown on TSA sheep blood agar plates (PML Microbiologicals, Mississauga, Ontario) at 37° C. for 18 hours, or in Todd-Hewitt broth (Oxoid Ltd., Hampshire, England) supplemented with 0.3% yeast extract (Sigma, St. Louis, Mo.) (THB-YE) at 37° C., 5% $CO_2$.

Chromosomal DNA was prepared from *S. dysgalactiae* grown in 100 ml of THB-YE supplemented with 20 mM glycine for approximately 6 hours, until an $A_{600}$ of 0.8 to 1.0 was reached. Cells were harvested and re-suspended in 50 mM EDTA, 50 mM Tris-HCl, 0.5% TWEEN-20 (Sigma, St. Louis, Mo.) and supplemented with RNase A (200 mg/ml), proteinase K (20 mg/ml), lysozyme (100 mg/ml) and mutanolysin (100 mg/ml). (Sigma, St. Louis, Mo.). Following bacterial lysis for 30 minutes at 37° C. with vigorous shaking, guanidine hydrochloride and TWEEN-20, pH 5.5, were mixed with the lysate to give a final concentration of 0.8 M and 5%, respectively. This mixture was incubated at 50° C. for 30 minutes. The chromosomal DNA was then purified using a Qiagen genomic-tip 100 g (Qiagen, Germany) and precipitated using 0.7 volumes of isopropanol. The resulting pellet was washed in 70% ethanol and re-suspended in 0.5 ml 10 mM Tris-HCl, pH 8.8.

B. Amplification and Cloning of the *S. dysgalactiae* Mig Gene

The Mig gene was amplified by PCR (See Mullis et al., U.S. Pat. No. 4,683,195; Mullis, U.S. Pat. No. 4,683,202;) using the forward primer mig1 (SEQ ID NO:1, shown in Table 1) and the reverse primer mig1 (SEQ ID NO:2, shown in Table 1). In the sequences depicted in Table 1, underlining denotes nucleotides added to the original sequence, and bolding indicates the location of restriction endonuclease recognition sites.

TABLE 1

Tabulation of Sequences

| SEQUENCE ID NO: | SEQUENCE NAME | NUCLEOTIDE/AMINO ACID SEQUENCE |
|---|---|---|
| 1 | Primer mig1 | 5'-G CGG CCA TGG TAG AAA ATA CTA TAA CTG-3' |
| 2 | Primer mig1R | 5'-ACG CCC GGG TTA GTC TTC TTT ACG TTT-3' |
| 3 | Streptococcus dysgalactiae strain SDG8 mig gene | (see FIG. 1) |
| 4 | Streptococcus dysgalactiae strain SDG8 Mig protein | |
| 5 | Primer mig-3 | 5'-GTT GGC CTA GAT ATC ACA GAA TTA CAA-3' |
| 6 | Primer mig-4 | 5'-AAA GCA CCC GGG CCA GCC ATT ACT G-3' |
| 7 | Primer mig-6 | 5'-AGG TGC TTC CCA TGG AAC TGC CTG AAC T-3' |
| 8 | Primer mig-7 | 5'-GGC GAG AGT CTA GAA ACT AAA GCG AAA AAC-3' |
| 9 | Primer mig-8 | 5'-GCA ATC ACC AGG ATC CTC AGT AAC CAT TTC-3' |
| 10 | Primer mig-9 | 5'-CAG GCA GTT CAT ATG GAA GCA CCT ACA GT-3' |
| 11 | Primer mig-10 | 5'-TCC CGG AGT AGC ATT GTC AGT C-3' |
| 12 | Primer mig-11 | 5'-GCA GCG GTC CAT ATG CCT GTT GGC CTA GAT-3' |
| 13 | Primer mig-12 | 5'-GCC TGA ACT GGA TCC CTC AAC TGA TCT G-3' |
| 14 | Primer mig-13 | 5'-TTC CGT TGG ATC CTG CAA CTC CAA TTG-3' |
| 15 | Primer mig-14 | 5'-TAA GTC AAA AGC TTT GAC AAT TAG TCT T-3' |

PCR was carried out using Vent DNA polymerase (New England Biolabs, Mississauga, Ontario, Canada). 0.7 μg of *S. dysgalactiae* genomic DNA, 1 μM each of the mig1 (SEQ ID NO:1) mig1r (SEQ ID NO:2) primers (see above), 200 μM each of dATP, dCTP, dGTP and dTTP, 3 mM $MgSO_4$, 1×ThermoPol PCR buffer (New England Biolabs), and 2 units of Vent DNA Polymerase were combined. The reaction mix was then incubated for 3 cycles of 1 minute at 94° C., 3 minutes at 50° C., and 1 minute, 10 seconds at 72° C., followed by 27 cycles of 15 seconds at 95° C., 30 seconds at 55° C., 1 minute at 72° C., followed by a single cycle of 5 minutes at 72° C.

The mig PCR product obtained above and the expression vector pAA505 (VIDO, Saskatoon, Saskatchewan, Canada) were digested with the restriction enzymes NcoI and SmaI (Amersham Pharmacia, Quebec, Canada) according to the manufacturer's instructions, and the mig sequence was ligated into the same sites of the vector.

This construct was used to transform *E. coli* DH5 α (Life Technologies, Gaithersburg, Md.). The transformed *E. coli* DH5 α cells bearing the pAA505-mig vector construct were designated *E. coli* DH5 α pAA505Mig.

C. Nucleotide Sequence of the *S. dysgalactiae* mig Gene and the Corresponding Deduced Amino Acid Sequence The nucleotide sequence in both orientations of the mig gene was determined on an ABI 373 DNA automatic sequencer (Applied Biosystems) at the Plant Biotechnology Institute (PBI, Saskatoon, Saskatchewan, Canada) by using the multiple primers shown in Table 1 (Primers mig-2 through mig-14).

FIGS. 1A–1D depict the nucleotide coding sequence and the amino acid sequence, respectively for the *S. dysgalactiae* Mig protein (SEQ ID NO:3 and SEQ ID NO:4, respectively).

These sequences were then compared against known sequences via BLAST analysis. The search parameters used to analyze the nucleic acid sequence were as follows: Database: nt; Number of letters in database: 1,961,177,913; Number of sequences in database:614,801; Matrix: blastn matrix:1–3; Gap Penalties: Existence: 5, Extension:2. The results obtained showed that the *S. dysgalactiae* SD8 mig gene depicted in FIGS. 1A–1D is homologous to several known nucleotide sequences, e.g., there is 98% homology with the mig gene for *S. dysgalactiae* SC1 (Emb Accession No. Z29666.1 SDMIGSUP).

The search parameters used to analyze the amino acid sequence were as follows: Database: nr; Number of letters in database: 157,988,256; Number of Sequences in database: 503,479; Matrix: BLOSUM62; Gap Penalties: Existence:11, Extension: 1. The results obtained showed that the *S. dysgalactiae* SD8 mig amino acid sequence depicted in FIGS. 1A–1D is up to 89% homologous to several known amino acid sequences.

D. Expression and Purification of the Recombinant *S. dysgalactiae* Mig Protein

*E. coli* containing the construct prepared in Example 1B, supra, was grown in LB broth containing 100 μg/ml ampicillin to an $A_{600}$ of approximately 0.5. Expression of the Mig protein was then induced by the addition of 1 mM isopropyl-β,D-thiogalactoside (IPTG) (Sigma, St. Louis, Mo.). Following three hours incubation at 37° C., cells were harvested, washed in column buffer (50 mM sodium phosphate pH 8.0, 0.2 M NaCl) and lysed by sonication.

Approximately 40% of the recombinant protein was in the soluble fraction of the cell sonicate with a yield of approximately 50 mg of the recombinant protein per liter of culture volume, as determined using a DC Protein Assay kit (BioRad Laboratories, Mississauga, Ontario, Canada) with bovine serum albumin (Pierce, Rockford, Ill.) as a standard.

The recombinant Mig protein was purified by affinity chromatography using an agarose-IgG matrix, based upon the protein's ability to bind the Fc portion of the IgG molecule. The cell lysate was cleared by centrifugation and the soluble fraction was applied to a BLIgG agarose column (Sigma, St. Louis, Mo.). The column was washed with 10 column volumes of column buffer (50 mM sodium phosphate pH 8.0, 0.3 M NaCl), and the protein eluted with column buffer plus 0.1 M glycine, pH 2.5, yielding a homogeneous protein fraction with a Mig concentration of approximately 10–15 mg/ml. The eluate was dialyzed against 2,000 volumes of PBSA and stored at −20° C.

E. Characterization of the Recombinant Protein

Analysis of the purified protein by SDS-PAGE demonstrated 60% purity.

EXAMPLE 2

Immunization with Mig and Experimental Infection of Cattle

Vaccines were formulated to contain 50 mg/ml of affinity purified recombinant Mig or GapC in the oil-based adjuvant VSA3 (VIDO, Saskatoon, Saskatchewan, Canada). VSA3 is a combination of Emulsigen Plus™ (MVP Laboratories, Ralston, Nebr.) and Dimethyldioctadecyl ammonium bromide (Kodak, Rochester, N.Y.).

24 non-lactating Holsteins with no history of *S. dysgalactiae* infection were obtained from various farms in Saskatchewan, Canada. One week prior to vaccination, all animals were treated with Cepha-dry™ (300 mg per quarter; Ayerst Laboratories, Montreal, Canada), in order to clear any infection of the udders prior to the vaccination step.

Three groups of eight animals were immunized subcutaneously with two doses of vaccines containing Mig, GapC (a plasmin binding protein isolated from streptococcus bacteria that was evaluated simultaneously), or a placebo with a three-week interval between immunizations. Two weeks following the second immunization, animals were exposed to 650 colony forming units of *S. dysgalactiae* delivered into three quarters with an udder infusion cannula. The fourth quarter on each animal served as an un-infective control.

All animals were examined daily for clinical signs of disease and samples from all udder quarters were collected on each day. Samples were observed for consistency and somatic cell counts as well as bacterial numbers were determined.

EXAMPLE 3

Bacterial Colonization

Bacteria were enumerated by spreading serial dilutions ($10^0$ to $10^{-3}$) directly onto TSA sheep blood agar plates followed by overnight incubation at 37° C., 5% $CO_2$. Colonization is defined as >500 cfu/ml of the challenge organism recovered.

To confirm that the bacteria recovered from milk secretions were *S. dysgalactiae*, selected colonies recovered from each animal were tested using an API strep-20 test (bioMerieux SA, Hazelwood, Mo.) according to the manufacturer's instructions. This test is a standardized method which combines 20 biochemical assays for enzymatic activity and sugar fermentation, the results of which yield an analytical profile. The profile permits identification of the particular streptococcal species present by either referring to an analytical profile index or using identification software.

Figure 4:
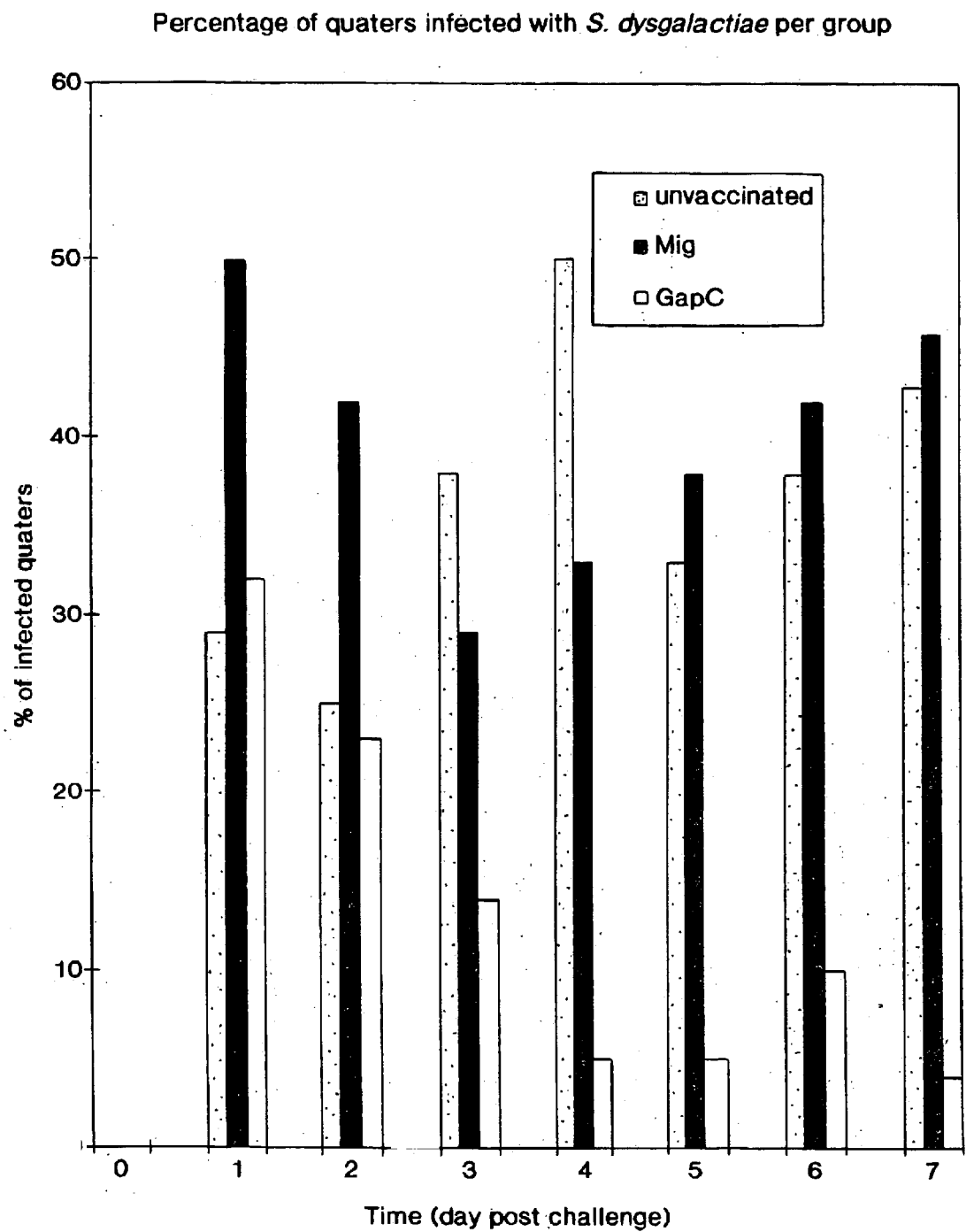
FIG. 4 compares the change in the percentage of udder quarters infected with *S. dysgalactiae* over a 7 day period among three experimental groups: (1) unvaccinated control animals; (2) animals vaccinated with the Mig protein; and (3) animals vaccinated with GapC, a plasmin binding protein isolated from *S. dysgalactiae* that was simultaneously evaluated. Infection was defined as recovery of >500 cfu of the *S. dysgalactiae* per ml of milk secretions.

Following challenge with *S. dysgalactiae*, animals from all groups were shown to be colonized by *S. dysgalactiae* (FIG. 4). The Mig-immunized animals showed a reduction in the number of infected quarters on days three and four post-challenge.

EXAMPLE 4

Measuring Inflammatory Response

Inflammatory response was measured as a function of somatic cell count (i.e., lymphocytes, neutrophils, and monocytes). Somatic cell counts were measured in a Coulter counter using standard techniques, as recommended by Agriculture and Agri-Food Canada Pamphlet IDF50B (1985) *Milk and Milk products—Methods of Sampling*. Samples were always read within 48 hours of collection and fixation.

Figure 5:
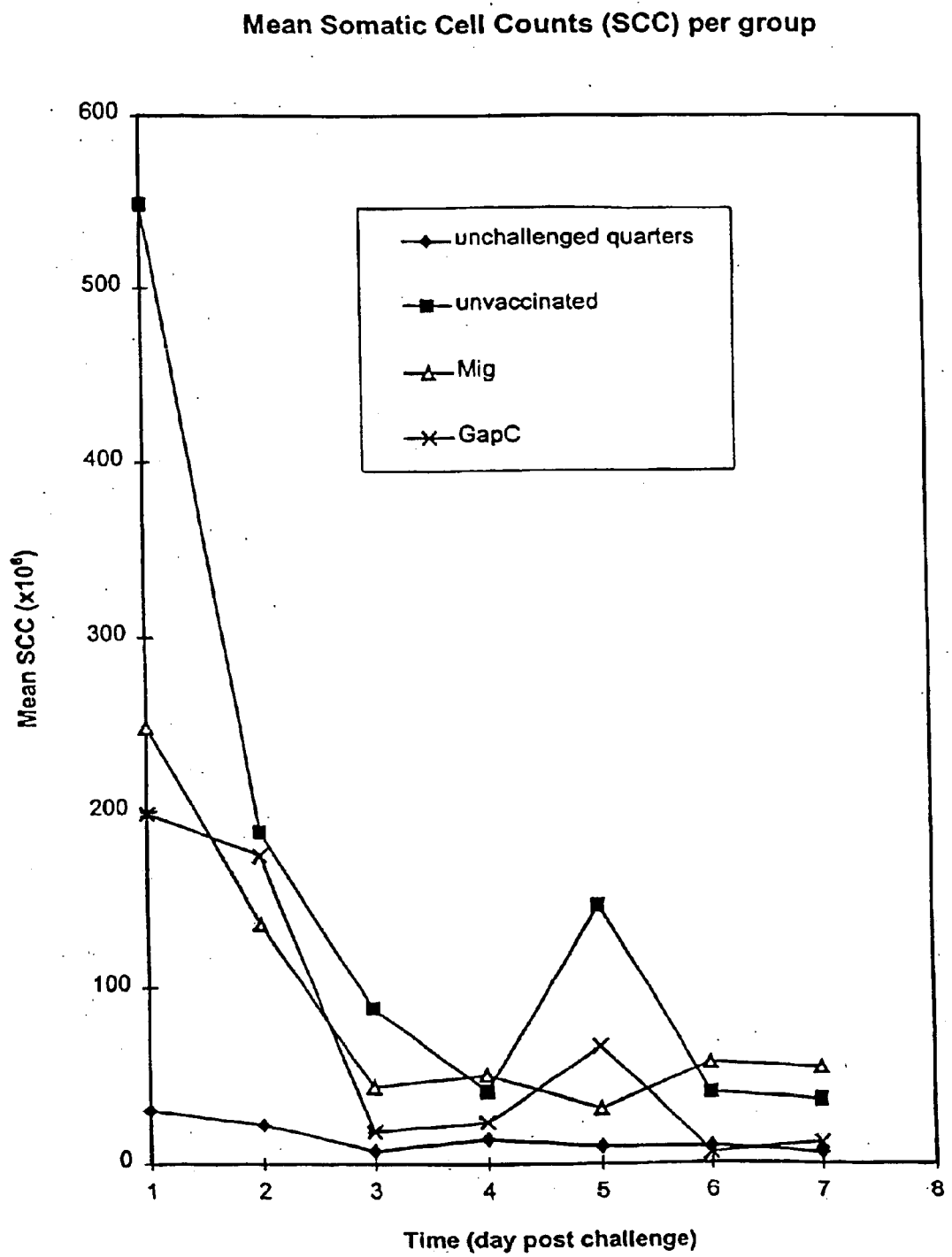
FIG. 5 depicts the observed inflammatory response to infection with *S. dysgalactiae* plotted as mean somatic cell counts (SCC) for each experimental group versus time in days post challenge. In the figure, diamonds (-♦-) represent unchallenged, unvaccinated quarters, squares (-■-) represent challenged, unvaccinated animals, triangles(-Δ-) represent challenged, Mig-vaccinated animals, and x's (-×-) represent challenged, GapC-vaccinated animals.
Figure 6:
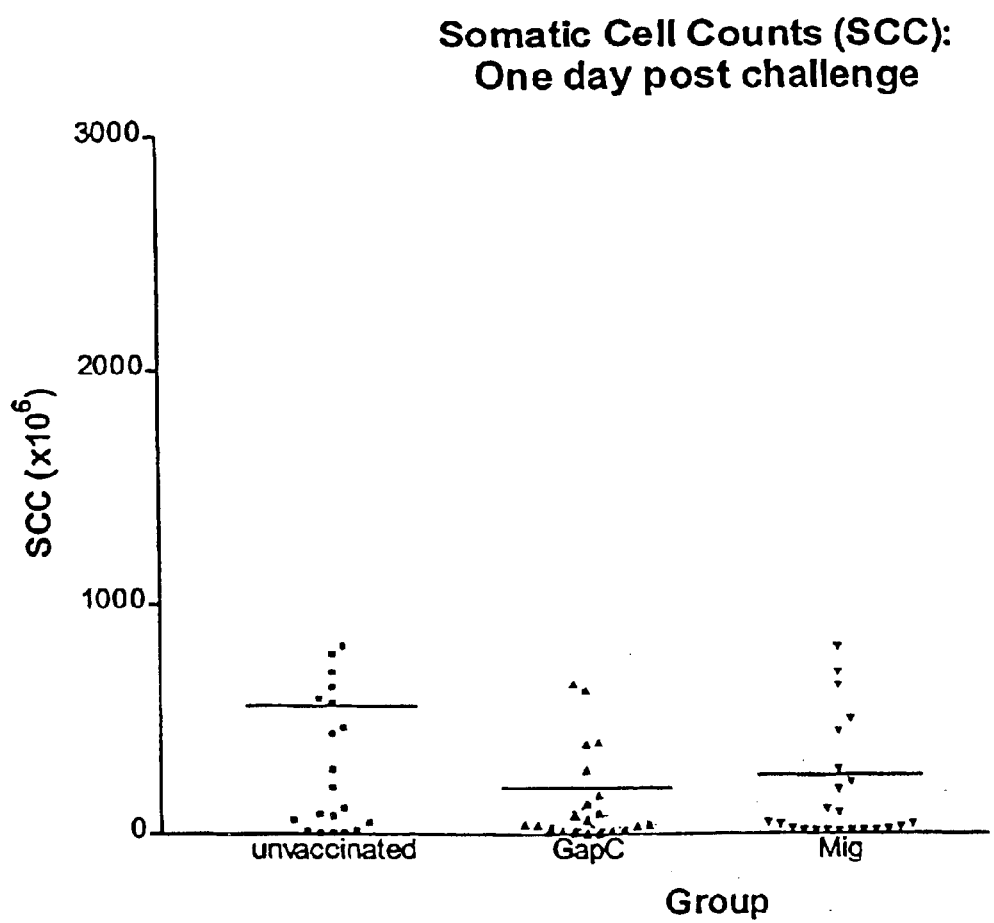
FIG. 6 illustrates somatic cell counts per mammary quarter on day 1 post-challenge. In the figure, the bar represents the mean for each group. Squares (-■-) represent unvaccinated animals; triangles (-Δ-) represent GapC-vaccinated animals, and inverted triangles (-▼-) represent Mig-vaccinated animals.

The number of somatic cells present in the gland was determined at days 1 through 7 post-challenge. Numbers from the unchallenged quarter remained constant throughout the trial, while on day 1, the Mig-immunized group was lower than the placebo-immunized group (FIG. 5). The individual data from day 1 is shown in FIG. 6.

Thus, the cloning, expression and characterization of the *S. dysgalactiae* Mig protein are disclosed, as are methods of using the same.

Although preferred embodiments of the subject invention have been described in some detail, it is understood that obvious variations can be made without departing from the spirit and the scope of the invention as defined by the appended claims.

What is claimed is:

1. An immunogenic composition comprising a *Streptococcus dysgalactiae* Mig protein, wherein said Mig protein comprises the amino acid sequence of the *Streptococcus dysgalactiae* Mig protein depicted at amino acid positions 1 to 669, inclusive, of FIGS. 1A–1D (SEQ ID NO:4).

2. The immunogenic composition of claim 1, wherein said Mig protein consists of the amino acid sequence of the *Streptococcus dysgalactiae* Mig protein depicted at amino acid positions 1 to 669, inclusive, of FIGS. 1A–1D (SEQ ID NO:4).

3. The immunogenic composition of claim 1, further comprising an adjuvant.

4. The immunogenic composition of claim 2, further comprising an adjuvant.

* * * * *

SEQUENCE LISTING

<160> NUMBER OF SEQ ID NOS: 15

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: primer mig1

<400> SEQUENCE: 1
gcggccatgg tagaaaatac tataactg                                              28

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: primer
      mig1R

<400> SEQUENCE: 2
acgcccgggt tagtcttctt tacgttt                                               27

<210> SEQ ID NO 3
<211> LENGTH: 2010
<212> TYPE: DNA
<213> ORGANISM: Streptococcus dysgalactiae
<220> FEATURE:
<221> NAME/KEY: CDS
<222> LOCATION: (1)..(2010)

<400> SEQUENCE: 3

```
atg gaa aaa gaa aaa aaa gta aaa tac ttt tta cgt aaa tca gct ttt        48
Met Glu Lys Glu Lys Lys Val Lys Tyr Phe Leu Arg Lys Ser Ala Phe
  1               5                  10                  15 gga tta gcg tct gta tca gct gcg ttt tta gtt tcg gga gca cta gaa        96
Gly Leu Ala Ser Val Ser Ala Ala Phe Leu Val Ser Gly Ala Leu Glu
             20                  25                  30 aat act ata act gtt tct gca gaa act ata cct gca gcg gtc att gta       144
Asn Thr Ile Thr Val Ser Ala Glu Thr Ile Pro Ala Ala Val Ile Val
         35                  40                  45 cct gtt ggc cta gat act aca gaa tta caa aaa tgg tat gac att gca       192
Pro Val Gly Leu Asp Thr Thr Glu Leu Gln Lys Trp Tyr Asp Ile Ala
     50                  55                  60 aat gat tta gtt gcg act gac aat gct act ccg gga ggc gta ttt aca       240
Asn Asp Leu Val Ala Thr Asp Asn Ala Thr Pro Gly Gly Val Phe Thr
 65                  70                  75                  80 gca gac tca atg aag gca tta tat cgt tta cta aat gat gca tac gat       288
Ala Asp Ser Met Lys Ala Leu Tyr Arg Leu Leu Asn Asp Ala Tyr Asp
                 85                  90                  95 gtg ttg gaa tca aaa gac tat aga aaa tat gat tct caa gat agg att       336
```

```
Val Leu Glu Ser Lys Asp Tyr Arg Lys Tyr Asp Ser Gln Asp Arg Ile
            100                 105                 110 gtt gaa ttg gta aac aat tta aag aat act acg cag tct ctt tta cca      384
Val Glu Leu Val Asn Asn Leu Lys Asn Thr Thr Gln Ser Leu Leu Pro
            115                 120                 125 att gga gta gaa cca gta gta ttt gat act act cgc ttg aat acc tgg      432
Ile Gly Val Glu Pro Val Val Phe Asp Thr Thr Arg Leu Asn Thr Trp
    130                 135                 140 tat gat gct gct aat gaa att gtt aat aat tca gat gct tat aca gca      480
Tyr Asp Ala Ala Asn Glu Ile Val Asn Asn Ser Asp Ala Tyr Thr Ala
145                 150                 155                 160 gaa tca att cag tcg ttg tat aag tta att aat gat gca tac gat gtg      528
Glu Ser Ile Gln Ser Leu Tyr Lys Leu Ile Asn Asp Ala Tyr Asp Val
                165                 170                 175 tta gaa tca aaa gat tac agt aag tat gat tct caa gat aaa gtc aac      576
Leu Glu Ser Lys Asp Tyr Ser Lys Tyr Asp Ser Gln Asp Lys Val Asn
            180                 185                 190 aat ctt gca gat cag ttg aga gat gca gtt cag gca gtt caa cta gaa      624
Asn Leu Ala Asp Gln Leu Arg Asp Ala Val Gln Ala Val Gln Leu Glu
        195                 200                 205 gca cct aca gtg att gac gca cct gaa cta act cca gct ttg act act      672
Ala Pro Thr Val Ile Asp Ala Pro Glu Leu Thr Pro Ala Leu Thr Thr
    210                 215                 220 tac aaa ctt gtt gtt aaa ggt aac act ttc tca gga gaa aca act act      720
Tyr Lys Leu Val Val Lys Gly Asn Thr Phe Ser Gly Glu Thr Thr Thr
225                 230                 235                 240 aaa gcc atc gat act gca act gcg gaa aaa gaa ttc aaa caa tac gca      768
Lys Ala Ile Asp Thr Ala Thr Ala Glu Lys Glu Phe Lys Gln Tyr Ala
                245                 250                 255 aca gct aac aat gtt gac ggt gag tgg tct tat gac gat gca act aaa      816
Thr Ala Asn Asn Val Asp Gly Glu Trp Ser Tyr Asp Asp Ala Thr Lys
            260                 265                 270 acc ttt aca gtt act gaa aaa cca gca gtg att gac gca ctt gaa cta      864
Thr Phe Thr Val Thr Glu Lys Pro Ala Val Ile Asp Ala Leu Glu Leu
        275                 280                 285 act cca gcc ttg act act tac aaa ctt att gtt aaa ggt aac act ttc      912
Thr Pro Ala Leu Thr Thr Tyr Lys Leu Ile Val Lys Gly Asn Thr Phe
    290                 295                 300 tca ggc gaa aca act act aaa gct atc gat gct gca act gca gaa aaa      960
Ser Gly Glu Thr Thr Thr Lys Ala Ile Asp Ala Ala Thr Ala Glu Lys
305                 310                 315                 320 gaa ttc aaa caa tac gca aca gct aac aat gtt gac ggt gag tgg tct     1008
Glu Phe Lys Gln Tyr Ala Thr Ala Asn Asn Val Asp Gly Glu Trp Ser
                325                 330                 335 tat gac tat gca act aaa acc ttt aca gtt act gaa aaa cca gca gtg     1056
Tyr Asp Tyr Ala Thr Lys Thr Phe Thr Val Thr Glu Lys Pro Ala Val
            340                 345                 350 att gac gca cct gaa cta act cca gcc ttg act act tac aaa ctt att     1104
Ile Asp Ala Pro Glu Leu Thr Pro Ala Leu Thr Thr Tyr Lys Leu Ile
        355                 360                 365 gtt aaa ggt aac act ttc tca ggc gaa aca act act aaa gct atc gat     1152
Val Lys Gly Asn Thr Phe Ser Gly Glu Thr Thr Thr Lys Ala Ile Asp
    370                 375                 380 gct gca act gca gaa aaa gaa ttc aaa caa tac gca aca gct aac aat     1200
Ala Ala Thr Ala Glu Lys Glu Phe Lys Gln Tyr Ala Thr Ala Asn Asn
385                 390                 395                 400 gtt gac ggt gaa tgg tct tat gac gat gca act aaa acc ttt aca gtt     1248
Val Asp Gly Glu Trp Ser Tyr Asp Asp Ala Thr Lys Thr Phe Thr Val
                405                 410                 415
```

```
act gaa aaa cca gca gtg att gac gca cct gaa cta act cca gcc ttg      1296
Thr Glu Lys Pro Ala Val Ile Asp Ala Pro Glu Leu Thr Pro Ala Leu
        420                 425                 430 act act tac aaa ctt att gtt aaa ggt aac act ttc tca ggc gaa aca      1344
Thr Thr Tyr Lys Leu Ile Val Lys Gly Asn Thr Phe Ser Gly Glu Thr
            435                 440                 445 act act aaa gca gta gac gca gaa act gca gaa aaa gcc ttc aaa caa      1392
Thr Thr Lys Ala Val Asp Ala Glu Thr Ala Glu Lys Ala Phe Lys Gln
        450                 455                 460 tac gca aca gct aac aat gtt gac ggt gaa tgg tct tat gac gat gca      1440
Tyr Ala Thr Ala Asn Asn Val Asp Gly Glu Trp Ser Tyr Asp Asp Ala
465                 470                 475                 480 act aaa acc ttt aca gtt act gaa aaa cca gca gtg att gac gca cct      1488
Thr Lys Thr Phe Thr Val Thr Glu Lys Pro Ala Val Ile Asp Ala Pro
            485                 490                 495 gaa tta aca cca gca ttg aca acc tac aaa ctt gtt atc aat ggt aaa      1536
Glu Leu Thr Pro Ala Leu Thr Thr Tyr Lys Leu Val Ile Asn Gly Lys
        500                 505                 510 aca ttg aaa ggc gaa aca act act aaa gca gta gac gta gaa act gca      1584
Thr Leu Lys Gly Glu Thr Thr Thr Lys Ala Val Asp Val Glu Thr Ala
            515                 520                 525 gaa aaa gcc ttc aaa caa tac gct aac gaa aac ggt gtt gat ggt gtt      1632
Glu Lys Ala Phe Lys Gln Tyr Ala Asn Glu Asn Gly Val Asp Gly Val
        530                 535                 540 tgg act tac gat gat gcg act aag acc ttt acg gta act gaa atg gtt      1680
Trp Thr Tyr Asp Asp Ala Thr Lys Thr Phe Thr Val Thr Glu Met Val
545                 550                 555                 560 act gaa att cct ggt gat gca cca act gaa cca gaa aag cca gaa gca      1728
Thr Glu Ile Pro Gly Asp Ala Pro Thr Glu Pro Glu Lys Pro Glu Ala
            565                 570                 575 agt atc cct ctt gtt ccg tta act cct gca act cca att gct aaa gat      1776
Ser Ile Pro Leu Val Pro Leu Thr Pro Ala Thr Pro Ile Ala Lys Asp
        580                 585                 590 gac gct aag aaa gac gat act aag aaa gtc gat act aag aaa gaa gac      1824
Asp Ala Lys Lys Asp Asp Thr Lys Lys Val Asp Thr Lys Lys Glu Asp
            595                 600                 605 gct aaa aaa cca gaa gct aaa aaa cca gaa gct aag aaa gaa gaa gct      1872
Ala Lys Lys Pro Glu Ala Lys Lys Pro Glu Ala Lys Lys Glu Glu Ala
        610                 615                 620 aag aaa gaa gaa gct aag aaa gct gca act ctt cct aca act ggt gaa      1920
Lys Lys Glu Glu Ala Lys Lys Ala Ala Thr Leu Pro Thr Thr Gly Glu
625                 630                 635                 640 gga agc aac cca ttt ttc aca gct gct gcg ctt gca gta atg gct ggt      1968
Gly Ser Asn Pro Phe Phe Thr Ala Ala Ala Leu Ala Val Met Ala Gly
            645                 650                 655 gcg ggt gct ttg gca gtc gct tca aaa cgt aaa gaa gac taa             2010
Ala Gly Ala Leu Ala Val Ala Ser Lys Arg Lys Glu Asp
        660                 665                 670

<210> SEQ ID NO 4
<211> LENGTH: 669
<212> TYPE: PRT
<213> ORGANISM: Streptococcus dysgalactiae

<400> SEQUENCE: 4

Met Glu Lys Glu Lys Lys Val Lys Tyr Phe Leu Arg Lys Ser Ala Phe
 1               5                  10                  15

Gly Leu Ala Ser Val Ser Ala Ala Phe Leu Val Ser Gly Ala Leu Glu
            20                  25                  30

Asn Thr Ile Thr Val Ser Ala Glu Thr Ile Pro Ala Ala Val Ile Val
```

```
                35              40              45
Pro Val Gly Leu Asp Thr Thr Glu Leu Gln Lys Trp Tyr Asp Ile Ala
             50              55              60

Asn Asp Leu Val Ala Thr Asp Asn Ala Thr Pro Gly Gly Val Phe Thr
 65              70              75              80

Ala Asp Ser Met Lys Ala Leu Tyr Arg Leu Leu Asn Asp Ala Tyr Asp
                 85              90              95

Val Leu Glu Ser Lys Asp Tyr Arg Lys Tyr Asp Ser Gln Asp Arg Ile
            100             105             110

Val Glu Leu Val Asn Asn Leu Lys Asn Thr Thr Gln Ser Leu Leu Pro
        115             120             125

Ile Gly Val Glu Pro Val Val Phe Asp Thr Thr Arg Leu Asn Thr Trp
130             135             140

Tyr Asp Ala Ala Asn Glu Ile Val Asn Asn Ser Asp Ala Tyr Thr Ala
145             150             155             160

Glu Ser Ile Gln Ser Leu Tyr Lys Leu Ile Asn Asp Ala Tyr Asp Val
            165             170             175

Leu Glu Ser Lys Asp Tyr Ser Lys Tyr Asp Ser Gln Asp Lys Val Asn
            180             185             190

Asn Leu Ala Asp Gln Leu Arg Asp Ala Val Gln Ala Val Gln Leu Glu
        195             200             205

Ala Pro Thr Val Ile Asp Ala Pro Glu Leu Thr Pro Ala Leu Thr Thr
        210             215             220

Tyr Lys Leu Val Val Lys Gly Asn Thr Phe Ser Gly Glu Thr Thr Thr
225             230             235             240

Lys Ala Ile Asp Thr Ala Thr Ala Glu Lys Glu Phe Lys Gln Tyr Ala
            245             250             255

Thr Ala Asn Asn Val Asp Gly Glu Trp Ser Tyr Asp Asp Ala Thr Lys
            260             265             270

Thr Phe Thr Val Thr Glu Lys Pro Ala Val Ile Asp Ala Leu Glu Leu
        275             280             285

Thr Pro Ala Leu Thr Thr Tyr Lys Leu Ile Val Lys Gly Asn Thr Phe
        290             295             300

Ser Gly Glu Thr Thr Thr Lys Ala Ile Asp Ala Ala Thr Ala Glu Lys
305             310             315             320

Glu Phe Lys Gln Tyr Ala Thr Ala Asn Asn Val Asp Gly Glu Trp Ser
            325             330             335

Tyr Asp Tyr Ala Thr Lys Thr Phe Thr Val Thr Glu Lys Pro Ala Val
            340             345             350

Ile Asp Ala Pro Glu Leu Thr Pro Ala Leu Thr Thr Tyr Lys Leu Ile
        355             360             365

Val Lys Gly Asn Thr Phe Ser Gly Glu Thr Thr Thr Lys Ala Ile Asp
370             375             380

Ala Ala Thr Ala Glu Lys Glu Phe Lys Gln Tyr Ala Thr Ala Asn Asn
385             390             395             400

Val Asp Gly Glu Trp Ser Tyr Asp Asp Ala Thr Lys Thr Phe Thr Val
            405             410             415

Thr Glu Lys Pro Ala Val Ile Asp Ala Pro Glu Leu Thr Pro Ala Leu
        420             425             430

Thr Thr Tyr Lys Leu Ile Val Lys Gly Asn Thr Phe Ser Gly Glu Thr
        435             440             445

Thr Thr Lys Ala Val Asp Ala Glu Thr Ala Glu Lys Ala Phe Lys Gln
450             455             460
```

-continued

```
Tyr Ala Thr Ala Asn Asn Val Asp Gly Glu Trp Ser Tyr Asp Asp Ala
465                 470                 475                 480
Thr Lys Thr Phe Thr Val Thr Glu Lys Pro Ala Val Ile Asp Ala Pro
            485                 490                 495
Glu Leu Thr Pro Ala Leu Thr Tyr Lys Leu Val Ile Asn Gly Lys
        500                 505                 510
Thr Leu Lys Gly Glu Thr Thr Lys Ala Val Asp Val Glu Thr Ala
        515                 520                 525
Glu Lys Ala Phe Lys Gln Tyr Ala Asn Glu Asn Gly Val Asp Gly Val
        530                 535                 540
Trp Thr Tyr Asp Asp Ala Thr Lys Thr Phe Thr Val Thr Glu Met Val
545                 550                 555                 560
Thr Glu Ile Pro Gly Asp Ala Pro Thr Glu Pro Glu Lys Pro Glu Ala
                565                 570                 575
Ser Ile Pro Leu Val Pro Leu Thr Pro Ala Thr Pro Ile Ala Lys Asp
                580                 585                 590
Asp Ala Lys Lys Asp Asp Thr Lys Lys Val Asp Thr Lys Lys Glu Asp
            595                 600                 605
Ala Lys Lys Pro Glu Ala Lys Lys Pro Glu Ala Lys Lys Glu Glu Ala
        610                 615                 620
Lys Lys Glu Glu Ala Lys Lys Ala Ala Thr Leu Pro Thr Thr Gly Glu
625                 630                 635                 640
Gly Ser Asn Pro Phe Phe Thr Ala Ala Leu Ala Val Met Ala Gly
                645                 650                 655
Ala Gly Ala Leu Ala Val Ala Ser Lys Arg Lys Glu Asp
        660                 665

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: primer
      mig-3

<400> SEQUENCE: 5
gttggcctag atatcacaga attacaa                                        27

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: primer
      mig-4

<400> SEQUENCE: 6
aaagcacccg ggccagccat tactg                                          25

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: primer
      mig-6

<400> SEQUENCE: 7
aggtgcttcc catggaactg cctgaact                                       28
```

```
<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: primer
      mig-7

<400> SEQUENCE: 8
ggcgagagtc tagaaactaa agcgaaaaac                                     30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: primer
      mig-8

<400> SEQUENCE: 9
gcaatcacca ggatcctcag taaccatttc                                     30

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: primer
      mig-9

<400> SEQUENCE: 10
caggcaggtc atatggaagc acctacagt                                      29

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: primer
      mig-10

<400> SEQUENCE: 11
tcccggagta gcattgtcag tc                                             22

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: primer
      mig-11

<400> SEQUENCE: 12
gcagcggtcc atatgcctgt tggcctagat                                     30

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: primer
      mig-12

<400> SEQUENCE: 13
gcctgaactg gatccctcaa ctgatctg                                       28
```

```
<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: primer
      mig-13

<400> SEQUENCE: 14
ttccgttgga tcctgcaact ccaattg                                          27

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: primer
      mig-14

<400> SEQUENCE: 15
taagtcaaaa gctttgacaa ttagtctt                                         28
```